US009918915B2

(12) United States Patent
Haught et al.

(10) Patent No.: US 9,918,915 B2
(45) Date of Patent: Mar. 20, 2018

(54) PERSONAL CARE COMPOSITIONS PROVIDING ENHANCED COOLING SENSATION

(75) Inventors: John Christian Haught, West Chester, OH (US); William Michael Glandorf, Mason, OH (US); Christine Lula Johnson, Germantown, OH (US); Lowell Alan Sanker, Cincinnati, OH (US)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 1200 days.

(21) Appl. No.: 12/636,096

(22) Filed: Dec. 11, 2009

(65) Prior Publication Data

US 2010/0086498 A1 Apr. 8, 2010

Related U.S. Application Data

(63) Continuation-in-part of application No. 12/274,467, filed on Nov. 20, 2008, now abandoned.

(60) Provisional application No. 61/003,863, filed on Nov. 20, 2007.

(51) Int. Cl.
| *A61Q 11/00* | (2006.01) |
| *A61K 8/00* | (2006.01) |
| *A61K 8/30* | (2006.01) |
| *A61K 8/35* | (2006.01) |
| *A61K 8/42* | (2006.01) |
| *A61K 8/34* | (2006.01) |
| *A61K 8/19* | (2006.01) |
| *A61K 8/37* | (2006.01) |
| *A61K 8/41* | (2006.01) |
| *A61K 8/49* | (2006.01) |
| *A61K 8/20* | (2006.01) |
| *A61K 8/22* | (2006.01) |
| *A61K 8/24* | (2006.01) |
| *A61K 8/55* | (2006.01) |

(52) U.S. Cl.
CPC ............... *A61K 8/345* (2013.01); *A61K 8/19* (2013.01); *A61K 8/20* (2013.01); *A61K 8/22* (2013.01); *A61K 8/24* (2013.01); *A61K 8/347* (2013.01); *A61K 8/37* (2013.01); *A61K 8/41* (2013.01); *A61K 8/42* (2013.01); *A61K 8/4973* (2013.01); *A61K 8/55* (2013.01); *A61Q 11/00* (2013.01); *A61K 2800/244* (2013.01)

(58) Field of Classification Search
None
See application file for complete search history.

(56) References Cited

U.S. PATENT DOCUMENTS

| 3,111,127 A | 11/1963 | Jarboe |
| 3,917,613 A | 11/1975 | Humbert et al. |
| 3,991,178 A | 11/1976 | Humbert et al. |
| 4,029,759 A | 6/1977 | Humbert et al. |
| 4,136,163 A | 1/1979 | Watson et al. |
| 4,150,052 A | 4/1979 | Watson et al. |
| 4,153,679 A | 5/1979 | Rowsell et al. |
| 4,157,384 A | 6/1979 | Watson et al. |
| 4,178,459 A | 12/1979 | Watson et al. |
| 4,230,688 A | 10/1980 | Rowsell et al. |
| 4,459,425 A | 7/1984 | Amano et al. |
| 5,266,592 A | 11/1993 | Grub et al. |
| 5,451,404 A | 9/1995 | Furman |
| 5,608,119 A | 3/1997 | Amano et al. |
| 5,703,123 A | 12/1997 | Pelzer et al. |
| 5,725,865 A | 3/1998 | Mane et al. |
| 5,843,466 A | 12/1998 | Mane et al. |
| 5,977,166 A | 11/1999 | Greenberg |
| 6,365,215 B1 | 4/2002 | Grainger et al. |
| 6,451,844 B1 | 9/2002 | Watkins et al. |
| 6,884,903 B2 | 4/2005 | Lorenz et al. |

(Continued)

FOREIGN PATENT DOCUMENTS

| EP | 310 299 | 4/1989 |
| GB | 1315626 | 3/1973 |

(Continued)

OTHER PUBLICATIONS

Eccles, R. "Menthol and Related Cooling Compounds", J. Pharm. Pharmacol., 46, pp. 618-630, 1994.

Emberger, R. et al., "Synthesis and Sensory Characterization of Menthol Enantiomers and Their Derivatives for the Use in Nature Identical Peppermint Oils," Specialty Chemicals, 7(3), 193-201, 1987.

Givaudan, S.A., "Compounds and Oral Care Compositions in Which They Are Used", Research Disclosure, vol. 522, No. 4, Oct. 1, 2007, p. 983.

International Search Report for PCT/US2009/053633.

(Continued)

*Primary Examiner* — Lezah Roberts

(57) ABSTRACT

Disclosed are personal care compositions for use on hair, skin, oral cavity, throat and other mucosal surfaces containing a flavor/perfume system comprising one or more coolants, wherein the pleasant cool and refreshing sensation provided by the coolant is enhanced in terms of quicker onset, greater intensity or impact and/or longer duration, thereby improving appeal and acceptability of the compositions to consumers. In one embodiment the invention provides oral care compositions comprising
(a) a flavor composition comprising one or more non-menthol coolants and optionally one or more additional flavor ingredients,
(b) a calcium ion source and/or a calcium transport agent sufficient to potentiate and/or modulate the cooling and refreshing sensation provided by the coolant(s), and
(c) an orally-acceptable carrier.

Upon application to the oral cavity, the compositions provide an immediate onset of cooling sensation which lasts longer than about 15 minutes thereby providing long-lasting clean and fresh mouth impression and encouraging user compliance and repeated use of the compositions.

8 Claims, No Drawings

(56) References Cited

U.S. PATENT DOCUMENTS

| | | | |
|---|---|---|---|
| 6,956,139 B2 | 10/2005 | Green et al. | |
| 7,189,760 B2 | 3/2007 | Erman et al. | |
| 2003/0129144 A1* | 7/2003 | Scott et al. | 424/48 |
| 2006/0134020 A1* | 6/2006 | Robinson et al. | 424/52 |
| 2007/0059417 A1 | 3/2007 | Moza et al. | |
| 2007/0231278 A1* | 10/2007 | Lee et al. | 424/53 |
| 2010/0040563 A1 | 2/2010 | Haught et al. | |
| 2010/0076080 A1 | 3/2010 | Yelm et al. | |

FOREIGN PATENT DOCUMENTS

| | | |
|---|---|---|
| WO | WO 02/15692 | 2/2002 |
| WO | WO 04/037764 | 5/2004 |
| WO | WO 05/002582 | 1/2005 |
| WO | WO 05/049553 | 6/2005 |
| WO | WO 06/103401 | 10/2006 |
| WO | WO 08/124667 | 10/2008 |
| WO | WO 09/140783 A | 11/2009 |

OTHER PUBLICATIONS

International Search Report for PCT/US2009/053634.
Rovner, Sophie L., "Better Than Mint Medicinal Chemistry Methods Lead to New Cooling Compounds that are more potent and last longer than menthol", Chemical & Engineering News, 2007, 85(39), pp. 95-98/.
Watson, H.R. et al., New Compounds With the Menthol Cooling Effect, J. Soc. Cosmet. Chem., 29, pp. 185-200, 29, 1978.
Wei et al., "AG-3-5: a chemical producing sensations of cold", J. Pharm. Pharmacol., 1983, 35:110-112.

* cited by examiner

PERSONAL CARE COMPOSITIONS PROVIDING ENHANCED COOLING SENSATION

CROSS REFERENCE TO RELATED APPLICATIONS

This application is a continuation-in-part of U.S. application Ser. No. 12/274,467 filed Nov. 20, 2008 now abandoned, which claims the benefit of U.S. Provisional Application No. 61/003,863 filed on Nov. 20, 2007.

TECHNICAL FIELD

The present invention relates to personal care compositions such as oral care and skin care compositions containing a flavor/perfume system comprising one or more coolants, wherein the pleasant cool sensation provided by the coolant is enhanced in terms of quicker onset, greater intensity or impact and/or longer duration, thereby improving appeal and acceptability of the compositions to consumers. In particular for oral care products, taste and mouthfeel characteristics are important not only for consumer acceptability but also for compliance since use of these products may involve fairly long residence time in the mouth and repeated use for maximum efficacy.

BACKGROUND OF THE INVENTION

Oral care products such as dentifrice and mouthrinse are routinely used by consumers as part of their oral care hygiene regimens. It is well known that oral care products can provide both therapeutic and cosmetic hygiene benefits to consumers. Therapeutic benefits include caries prevention which is typically delivered through the use of various fluoride salts; gingivitis prevention by the use of an antimicrobial agent such as triclosan, stannous fluoride, or essential oils; or hypersensitivity control through the use of ingredients such as strontium chloride or potassium nitrate. Cosmetic benefits provided by oral care products include the control of plaque and calculus formation, removal and prevention of tooth stain, tooth whitening, breath freshening, and overall improvements in mouth feel impression which can be broadly characterized as mouth feel aesthetics. Calculus and plaque along with behavioral and environmental factors lead to formation of dental stains, significantly affecting the aesthetic appearance of teeth. Behavioral and environmental factors that contribute to teeth staining propensity include regular use of coffee, tea, cola or tobacco products, and also the use of certain oral products containing ingredients that promote staining, such as cationic antimicrobials and metal salts.

Thus daily oral care at home requires products with multiple ingredients working by different mechanisms to provide the complete range of therapeutic and aesthetic benefits, including anticaries, antimicrobial, antigingivitis, antiplaque, anticalculus and anti-erosion, as well as antiodor, mouth refreshment, stain removal, stain control and tooth whitening. In order for oral care products for daily use such as dentifrice and rinses to provide complete oral care it is necessary to combine actives and additives, many of which have the disadvantage of causing negative aesthetics during use, in particular unpleasant taste and sensations and stain promotion. The unpleasant taste and mouth sensations have been described as having one or more of bitter, metallic, astringent, salty, numbing, stinging, burning, prickling, and even irritating aspects. Typical ingredients for oral care use that are associated with these aesthetic negatives include antimicrobial agents such as cetyl pyridinium chloride, chlorhexidine, stannous and zinc salts; tooth bleaching agents such as peroxides; antitartar agents such as pyrophosphate, tripolyphosphate and hexametaphosphate; and excipients such as baking soda and surfactants. To mitigate the aesthetic negatives from these ingredients, oral care products are typically formulated with flavoring agents, sweeteners and coolants to taste as good as possible and provide a pleasant experience. In particular, it is desirable for oral care products to provide a refreshing cooling sensation during and after use.

Thus in one aspect, the present invention provides oral care compositions comprising a flavor system comprising traditional flavor components combined with one or a mixture of coolant chemicals wherein the cooling and refreshing sensation provided by the coolant(s) is potentiated in terms of onset, intensity or impact and/or duration.

SUMMARY OF THE INVENTION

The present invention is directed to personal care products intended for use on skin, hair, the oral cavity and other mucosal surfaces and to flavor or perfume compositions for use in such personal care products, comprising one or more coolants with enhanced activity. In one embodiment the invention provides oral care compositions comprising (a) a flavor composition comprising one or more coolants other than menthol and optionally one or more additional flavor ingredients, (b) a calcium ion source or a calcium transport agent sufficient to potentiate and/or modulate the cooling and refreshing sensation provided by the coolant(s), and (c) an orally-acceptable carrier.

Upon application to the oral cavity, the oral care compositions provide an immediate onset of cooling sensation which lasts longer than about 15 minutes thereby providing long-lasting clean and fresh mouth feel and encouraging user compliance and repeated use of the compositions.

These and other features, aspects, and advantages of the present invention will become evident to those skilled in the art from the detailed description which follows.

DETAILED DESCRIPTION OF THE INVENTION

While the specification concludes with claims particularly pointing out and distinctly claiming the invention, it is believed that the present invention will be better understood from the following description.

All percentages and ratios used hereinafter are by weight of total composition, unless otherwise indicated. All percentages, ratios, and levels of ingredients referred to herein are based on the actual amount of the ingredient, and do not include solvents, fillers, or other materials with which the ingredient may be combined as a commercially available product, unless otherwise indicated.

All measurements referred to herein are made at 25° C. unless otherwise specified.

Herein, the word "comprising" and its variants mean that other steps and other components which do not affect the end result can be added. These terms encompass the terms "consisting of" and "consisting essentially of."

As used herein, the word "include," and its variants, are intended to be non-limiting, such that recitation of items in a list is not to the exclusion of other like items that may also be useful in the materials, compositions, devices, and methods of this invention.

As used herein, the words "preferred", "preferably" and variants refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

By "oral care composition" is meant a product, which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity. The oral care composition may be in various forms including toothpaste, dentifrice, tooth gel, subgingival gel, mouthrinse, mousse, foam, mouthspray, lozenge, chewable tablet, chewing gum or denture product. The oral care composition may also be incorporated onto strips or films for direct application or attachment to oral surfaces.

The term "dentifrice", as used herein, includes paste, gel, or liquid formulations unless otherwise specified. The dentifrice composition may be a single phase composition or may be a combination of two or more separate dentifrice compositions. The dentifrice composition may be in any desired form, such as deep striped, surface striped, multilayered, having a gel surrounding a paste, or any combination thereof. Each dentifrice composition in a dentifrice comprising two or more separate dentifrice compositions may be contained in a physically separated compartment of a dispenser and dispensed side-by-side.

The term "dispenser", as used herein, means any pump, tube, or container suitable for dispensing compositions such as dentifrices.

The term "teeth", as used herein, refers to natural teeth as well as artificial teeth or dental prosthesis.

The term "orally acceptable carrier or excipients" includes safe and effective materials and conventional additives used in oral care compositions including but not limited to fluoride ion sources, anti-calculus or anti-tartar agents, buffers, abrasives such as silica, alkali metal bicarbonate salts, thickening materials, humectants, water, surfactants, titanium dioxide, flavorants, sweetening agents, xylitol, coloring agents, and mixtures thereof.

Active and other ingredients useful herein may be categorized or described herein by their cosmetic and/or therapeutic benefit or their postulated mode of action or function. However, it is to be understood that the active and other ingredients useful herein can, in some instances, provide more than one cosmetic and/or therapeutic benefit or function or operate via more than one mode of action. Therefore, classifications herein are made for the sake of convenience and are not intended to limit an ingredient to the particularly stated function(s) or activities listed.

Herein, the terms "tartar" and "calculus" are used interchangeably and refer to mineralized dental plaque biofilms.

The essential and optional components of the present compositions are described in the following paragraphs.

Coolant(s)

Coolants or compounds that have a physiological cooling effect particularly on oral and other mucosal surfaces and skin are common ingredients in a wide variety of products including edible compositions and personal care products and in flavor or perfume compositions for use in such products. Examples of edible compositions include confectionery, candies, chocolate, chewing gum, beverages and oral medicines. Compositions for topical application to the skin, hair and mucosal surfaces include lotions or creams, skin cleansers, shampoos and conditioners, wipes and towelettes and cosmetic products such as lipsticks and foundations. A particular class of topically applied compositions to which the present invention relates is for oral and throat care, which include products in powder, paste or liquid forms and which on being used are retained for a time sufficient to contact the surface and the internal mucous membrane of the oral or nasal cavities or the pharynx. Such products include for example, mouthwashes, dental and throat lozenges, gargles, chewing gum, dentifrice or toothpastes, toothpicks, dental tablets and powders and topical solutions for application in dental treatment, as well as cough-syrups, chewable antacids and digestion promoting preparations.

The pleasant cooling sensation provided by coolants contributes to the appeal and acceptability of the products. In particular, oral care products such as dentifrices and mouthwashes are formulated with coolants because they provide breath freshening effects and a clean, cool, fresh feeling in the mouth.

It is now well established that sensations such as cool or cold can be attributed to activation of receptors at peripheral nerve fibers by a stimulus such as low temperature or a chemical coolant, which produces electrochemical signals that travel to the brain, which then interprets, organizes and integrates the incoming signal(s) into a perception or sensation. Different classes of receptors have been implicated in sensing cold temperatures or chemical coolant stimuli at mammalian sensory nerve fibers. Among these receptors, a major candidate involved in sensing cold has been identified and designated as cold- and menthol-sensitive receptor (CMR1) or TRPM8. The TRPM8 nomenclature for the receptor comes from its characterization as a non-selective cation channel of the transient receptor potential (TRP) family that is activated by stimuli including low temperatures, menthol and other chemical coolants. However, the precise mechanisms underlying the perception of a pleasant cooling sensation on skin or oral surfaces are presently not clearly understood. While it has been demonstrated that the TRPM8 receptor is activated by menthol and other coolants, it is not fully understood what other receptors may be involved and to what extent these receptors need to be stimulated or perhaps suppressed in order that the overall perceived sensation would be pleasant, cooling and refreshing. For example, menthol is widely used as a cooling agent, but menthol can also produce other sensations including tingling, burning, prickling and stinging as well as a minty smell and bitter taste. Thus, it can be inferred that menthol acts on many different receptors, including cold, warm, pain and taste receptors. However, it is not readily discernible how to isolate which receptor activities would result in a specific sensation such as pleasant cooling without the undesirable sensations such as bitterness or irritation. Neither is it apparent how to control the activity of coolants or other sensory agents such that only the desired sensation is elicited from use of a particular sensory agent. The present invention is thus based on the discovery of agents that can be used to enhance and/or modulate the activity of sensory materials or "sensates", in particular coolant compounds such as described below.

A large number of coolant compounds of natural or synthetic origin have been described. The most well-known compound is menthol, particularly l-menthol, which is found naturally in peppermint oil, notably of *Mentha arvensis* L and *Mentha viridis* L. Of the isomers of menthol, the l-isomer occurs most widely in nature and is typically what is referred by the name menthol having coolant properties. L-menthol has the characteristic peppermint odor, has a clean fresh taste and exerts a cooling sensation when applied to the skin and mucosal surfaces. Other isomers of menthol (neomenthol, isomenthol and neoisomenthol) have somewhat similar, but not identical odor and taste, i.e., some having disagreeable notes described as earthy, camphor, musty. The biggest difference among the isomers is in their cooling potency. L-menthol provides the most potent cooling, i.e., having the lowest cooling threshold of about 800 ppb, i.e., the concentration where the cooling effect could be clearly recognized. At this level, there is no cooling effect for the other isomers. For example, d-neomenthol is reported to have a cooling threshold of about 25,000 ppb and l-neomenthol about 3,000 ppb. [R. Emberger and R. Hopp, "Synthesis and Sensory Characterization of Menthol Enantiomers and Their Derivatives for the Use in Nature Identical Peppermint Oils," Specialty Chemicals (1987), 7(3), 193-201]. This study demonstrated the outstanding sensory properties of l-menthol in terms or cooling and freshness and the influence of stereochemistry on the activity of these molecules.

Among synthetic coolants, many are derivatives of or are structurally related to menthol, i.e., containing the cyclohexane moiety, and derivatized with functional groups including carboxamide, ketal, ester, ether and alcohol. Examples include the ρ-menthanecarboxamide compounds such as N-ethyl-ρ-menthan-3-carboxamide, known commercially as "WS-3", and others in the series such as WS-5 (N-ethoxycarbonylmethyl-ρ-menthan-3-carboxamide), WS-12 [N-(4-methoxyphenyl)-ρ-menthan-3-carboxamide] and WS-14 (N-tert-butyl-ρ-menthan-3-carboxamide). Examples of menthane carboxy esters include WS-4 and WS-30. An example of a synthetic carboxamide coolant that is structurally unrelated to menthol is N,2,3-trimethyl-2-isopropylbutanamide, known as "WS-23". Additional examples of synthetic coolants include alcohol derivatives such as 3-(1-menthoxy)-propane-1,2-diol known as TK-10, isopulegol (under the tradename Coolact P) and ρ-menthane-3,8-diol (under the tradename Coolact 38D) all available from Takasago; menthone glycerol acetal known as MGA; menthyl esters such as menthyl acetate, menthyl acetoacetate, menthyl lactate known as Frescolat® supplied by Haarmann and Reimer, and monomenthyl succinate under the tradename Physcool from V. Mane. TK-10 is described in U.S. Pat. No. 4,459,425 to Amano et al. Other alcohol and ether derivatives of menthol are described e.g., in GB 1,315,626 and in U.S. Pat. Nos. 4,029,759; 5,608,119; and 6,956,139. WS-3 and other carboxamide cooling agents are described for example in U.S. Pat. Nos. 4,136,163; 4,150,052; 4,153,679; 4,157,384; 4,178,459 and 4,230,688Additional N-substituted ρ-menthane carboxamides are described in WO 2005/049553A1 including N-(4-cyanomethylphenyl)-ρ-menthanecarboxamide, N-(4-sulfamoylphenyl)-ρ-menthanecarboxamide, N-(4-cyanophenyl)$_p$-menthanecarboxamide, N-(4-acetylphenyl)-ρ-menthanecarboxamide, N-(4-hydroxymethylphenyl)-ρ-menthanecarboxamide and N-(3-hydroxy-4-methoxyphenyl)-ρ-menthanecarboxamide. Other N-substituted ρ-menthane carboxamides include amino acid derivatives such as those disclosed in WO 2006/103401 and in U.S. Pat. Nos. 4,136,163; 4,178,459 and 7,189,760 such as N-((5-methyl-2-(1-methylethyl)cyclohexyl)carbonyl)glycine ethyl ester and N-((5-methyl-2-(1-methylethyl)cyclohexyl)carbonyl)alanine ethyl ester. Menthyl esters including those of amino acids such as glycine and alanine are disclosed e.g., in EP 310,299 and in U.S. Pat. Nos. 3,111,127; 3,917,613; 3,991,178; 5,5703,123; 5,725,865; 5,843,466; 6,365,215; 6,451,844; and 6,884,903Ketal derivatives are described, e.g., in U.S. Pat. Nos. 5,266,592; 5,977,166 and 5,451,404Additional agents that are structurally unrelated to menthol but have been reported to have a similar physiological cooling effect include alpha-keto enamine derivatives described in U.S. Pat. No. 6,592,884 including 3-methyl-2-(1-pyrrolidinyl)-2-cyclopenten-1-one (3-MPC), 5-methyl-2-(1-pyrrolidinyl)-2-cyclopenten-1-one (5-MPC), and 2,5-dimethyl-4-(1-pyrrolidinyl)-3(2H)-furanone (DMPF); icilin (also known as AG-3-5chemical name 1-[2-hydroxyphenyl]-4-[2-nitrophenyl]-1,2,3,6-tetrahydropyrimidine-2-one) described in Wei et al., *J. Pharm. Pharmacol*(1983), 35:110-112Reviews on the coolant activity of menthol and synthetic coolants include H. R. Watson, et al. *J. Soc. Cosmet. Chem*(1978), 29, 185-200 and R. Eccles, *J. Pharm. Pharmacol*(1994), 46, 618-630.

Ideally, a coolant should produce a cooling or freshness sensation similar to that produced by menthol, but without certain of the disadvantages associated with menthol, such as flavor modification, bitter aftertaste, off-flavor, strong odor and burning or irritating sensation, particularly at high concentrations. It is desirable that the coolant compounds barely possess a distinctive odor or flavor while providing a pleasant fresh cool sensation of prolonged duration, in order that the effect can still be perceived for a considerable time after use, for example, longer than 15 minutes. Menthol generally provides an initial high cooling impact, but its effect is somewhat transient in that the cool sensation drops sharply within a few minutes after use. By contrast, a number of longer lasting coolant compounds may fail to provide an immediate cooling perception, i.e., within a few seconds of application, particularly when used at low levels. Thus there is a continuing need for means to potentiate the activity of coolant chemicals, in terms of quickening the onset of the cooling sensation, intensifying the cooling sensation especially at lower concentrations and producing a longer lasting sensation of cooling and freshness than what menthol provides.

The present invention relates to the discovery of such means to potentiate and/or modulate coolant agent activity described in the following paragraph.

Potentiation/Modulation of Coolant Activity

The present inventors have discovered that increasing calcium ion flux or mobilization in receptor cells enhance the activity of coolants in terms of onset, intensity or impact and duration. This discovery is particularly unexpected in view of previous reports on the effects of calcium in increasing activity of warm receptors and depressing activity of cold receptors. [H. Hensel and K. Schafer, "Effects of Calcium on Warm and Cold Receptors," *Pflugers Arch* (1974) 352: 87-90] Subsequent electrophysiological studies on warm and cold receptors in the nasal area of the cat by Schafer and others demonstrated that a decrease in external calcium concentration around receptors caused by administration of the calcium-chelating agent EDTA caused an increase in cold receptor activity. It has also been reported that decreasing calcium concentration enhanced cold receptor activity [*J. Neurophysiol*(1982) 47: 1017-1028*Physiol. Res*(1992) 41: 71-75]Further, intravenous injection of calcium solutions in man has been reported to cause a diffuse sensation of warmth [J. Hirschsohn and H. Maendl *Wien. Arch. Inn. Med*(1922) 4: 379-414]From these studies, it would be expected that the effect of calcium would be to inhibit coolant activity and to enhance activity of warming agents. The present discovery of the potentiating action of calcium on coolant activity is therefore surprising and unexpected.

As demonstrated in sensory studies described below, the potentiating action of calcium ions depends on a number of factors including calcium ion and coolant concentration, chemical nature of the coolant(s) and solubilization of the coolant(s) during use. It has also been found that the potentiating effect of calcium ions on coolants, particularly the synthetic menthane derivatives is further enhanced in the presence of menthol. Without wishing to be bound by theory, it is believed that menthol provides this enhancing effect because of its activity to immediately stimulate certain thermoreceptors and open up these ion channels for mobilization of calcium ions.

Sensory evaluation studies of coolant activity were conducted using a methodology patterned after the techniques described in M. C. Meilgaard, et al., *Sensory Evaluation Techniques*, 4$^{th}$ Ed. (2007). In one study, a panel of 11 trained sensory experts evaluated cooling sensation experienced after brushing with a dentifrice containing coolant(s) followed by rinsing with an aqueous rinse containing a calcium ion source. Panelists brushed teeth with 1.5 grams of a test dentifrice (containing coolant) or control (no coolant) and then expectorated. After brush expectoration, panelists evaluated cooling intensity, assigning a number between 0 (no cooling) to 60 (intense cooling). Panelists then rinsed mouth with 15 ml. of an aqueous rinse (with or without calcium) and expectorated. After rinse expectoration, panelists evaluated cooling intensity according to the same 0 to 60 scale. Evaluations were conducted at 5, 15, 30, 45, 60 minute, etc. time points. At each evaluation, panelists were instructed to breathe in through pursed lips and evaluate overall cooling sensation. In this test, a numerical score of 7.5 indicates meaningful or definite cooling. Results are summarized in Table 1 below.

effect is particularly evident with the coolants designated as MGA, chemically menthone glycerol acetal and the G-180 coolant, chemically N-(4-cyanomethylphenyl)-p-menthane-carboxamide, supplied by Givaudan as a 7.5% solution in flavor oil such as spearmint or peppermint. Addition of calcium ions elevated the cooling effect of a 75 ppm G-180 formula to that of a 150 ppm G-180 formula, which would enable formulating products with lower levels of coolant. This finding is particularly significant for coolants such as G-180 which panelists have described as providing a "burning" sensation particularly when used at higher levels. The calcium effect appears to be dose dependent, a higher level of calcium producing greater cooling enhancement at the concentrations tested for G-180However, as the data indicate, the effect is also dependent on the level and chemical structure of the coolant as well as the calcium to coolant weight ratio. For a number of the coolants studied, no significant potentiating effect of calcium was observed at the levels of coolant and calcium used. It is believed the calcium potentiating effect would be more apparent at low levels of coolant and at optimized calcium to coolant ratios. At high coolant levels, calcium may be providing more of a modulating effect, such as tempering harsh, burning, biting, or bitter sensations from the coolant(s). The calcium to coolant weight ratio is at least about 0.5 to 1preferably at least 1:1 or higher.

A calcium enhancing effect was also observed for MGA at the 1500 ppm level; i.e., cooling was observed at the 15 minute time point or beyond. For menthol at the 1500 ppm level, the same calcium enhancing effect was not observed. By contrast calcium extended the duration of G-180 cooling up to 60 minutes. However, combining menthol with calcium and G-180 raised the cooling intensity and the duration of the cooling experience, particularly at higher calcium to coolant ratios. In this regard, menthol is acting as a potentiating agent.

TABLE 1

Cooling Sensation Scores at Various Time Points After Application

| ppm Coolant in Paste | Ca$^{+2}$ ppm | Ca$^{+2}$/ Coolant | 0 min. | 5 min. | 15 min. | 30 min. | 45 min. | 60 min. |
| --- | --- | --- | --- | --- | --- | --- | --- | --- |
| 75 ppm G-180 | 0 | 0 | 21.1 | 23.7 | 22.9 | 15.0 | 11.0 | 5.8 |
| 75 ppm G-180 | 271 | 3.6 | 17.5 | 18.3 | 20.7 | 16.8 | 13.3 | 8.4 |
| 75 ppm G-180 | 542 | 7.2 | 18.8 | 25.0 | 29.2 | 24.4 | 18.6 | 14.1 |
| 150 ppm G-180 | 0 | 0 | 16.7 | 16.0 | 25.7 | 19.5 | 10.0 | 1.5 |
| 150 ppm G-180 | 271 | 1.8 | 12.1 | 22.5 | 26.0 | 17.1 | 11.2 | 0 |
| 150 ppm G-180 | 542 | 3.6 | 15.1 | 21.9 | 27.2 | 24.8 | 18.2 | 8.0 |
| 1000 ppm WS-3 | 0 | 0 | 26.2 | 25.4 | 11.3 | 0 | 0 | 0 |
| 1000 ppm WS-3 | 271 | 0.3 | 23.8 | 21.4 | 10.8 | 2.4 | 0 | 0 |
| 1000 ppm WS-3 | 542 | 0.5 | 23.6 | 14.0 | 0 | 0 | 0 | 0 |
| 1500 ppm WS-3 | 0 | 0 | 18.1 | 29.4 | 12.7 | 0 | 0 | 0 |
| 1500 ppm WS-3 | 271 | 0.2 | 20.0 | 29.8 | 9.5 | 1.1 | 0 | 0 |
| 1500 ppm WS-3 | 542 | 0.4 | 19.3 | 23.7 | 5.0 | 2.7 | 0 | 0 |
| 1500 ppm Menthol | 542 | 0.4 | 18.0 | 17.5 | 4.4 | 0 | 0 | 0 |
| 1500 ppm Menthol + 150 ppm G180 | 271 | 1.8 | 19.8 | 28.0 | 29.7 | 22.9 | 16.2 | 9.2 |
| 1500 ppm MGA | 0 | 0 | 16.5 | 13.6 | 4.4 | 0 | 0 | 0 |
| 1500 ppm MGA | 723 | 0.5 | 20.7 | 18.3 | 7.0 | 1.4 | 0 | 0 |
| 800 ppm WS-23 | 0 | 0 | 15.4 | 7.4 | 3.0 | 0 | 0 | 0 |
| 800 ppm WS-23 | 723 | 0.9 | 18.8 | 4.9 | 1.0 | 0 | 0 | 0 |
| 800 ppm WS-5 | 0 | 0 | 29.2 | 22.4 | 8.3 | 1.0 | 0 | 0 |
| 800 ppm WS-5 | 723 | 0.9 | 30.8 | 22.2 | 8.4 | 2.2 | 0 | 0 |
| 1000 ppm Menthyl Lactate | 0 | 0 | 23.0 | 12.7 | 2.3 | 0 | 0 | 0 |
| 1000 ppm Menthyl Lactate | 723 | 0.7 | 23.5 | 12.4 | 2.2 | 0 | 0 | 0 |

G-180 coolant supplied by Givaudan as 7.5% solution in spearmint oil.

Overall, providing calcium ions resulted in a potentiating effect particularly on cooling intensity and duration. This Addition of an external calcium ion source is one means of increasing calcium ion flux within receptor cells. The source of calcium ions may be any physiologically acceptable calcium compound including inorganic or organic salts such as halides (chloride, bromide, iodide, fluoride), nitrate, nitrite, phosphate, pyrophosphate, polyphosphate, sulfate, carbonate, hypochlorite, formate, acetate, citrate, lactate, maleate, gluconate, tartrate, glycerophosphate, butyrate, isobutyrate, oxalate, peptide, phosphopeptide or from oxides or hydroxides. The calcium ion source may be water soluble, sparingly-soluble or insoluble and can provide a minimum level of at least about 10 ppm calcium ions up to about 10,000 ppm for potentiating activity. Preferably the added calcium source provides at least about 50 ppm calcium ions, more preferably at least about 150 ppm to about 500 ppm. The level of the calcium ion source is of course also dependent on secondary considerations such as aesthetics and stability of the compositions. Some calcium compounds may alter the overall taste of the composition, for example being described as "chalky" and would thus not be desirable at levels that produce such effects.

Another means that has been found to increase calcium ion flux within receptors is by addition of calcium solubilizing agents, such as phosphate compounds, for example phytate, polyphosphate and organophosphates. It is believed that such compounds function as a calcium carrier or transport agent, bringing external calcium to the receptors or helping transport calcium ions released from intracellular calcium stores during coolant activation. The following studies compared the effects of various oral care formulation components on intracellular calcium ion ($Ca^{+2}$) levels in TRPM8 receptors.

In this study, HEK-23 (human embryonic kidney) cells stably transfected with human TRPM8 were grown in 15 ml growth medium [high glucose DMEM (Dulbecco's Modification of Eagle's Medium) supplemented with 10% FBS (fetal bovine serum), 100 ug/ml Penicillin/streptomycin, 5 μg/ml blasticindin, and 100 μg/ml zeocin) in a 75 $CM^2$ flask for 3 days at 37° C. in a mammalian cell culture incubator set at 5% $CO_2$ Cells were detached with addition of 2 ml of trypsin-EDTA buffer (GIBCO® 25200Invitrogen) for about 2-3 min. Trypsin was inactivated by addition of 8 ml growth medium. Cells were transferred to a 50 ml tube and centrifuged at 850 rpm for 3 minutes to remove medium. After centrifugation, a pellet of cells was formed in the bottom of the tube separating them from the supernatant solution. The supernatant was discarded and the cell pellet was suspended in 1 ml of fresh growth medium to which 5 ul (12.5 ug) of Fluo-4 AM (Molecular Probes, Inc.) calcium indicator was added and incubated for 30 min with gentle shaking. (Fluo-4 is a fluorescent dye used for quantifying cellular $Ca^{2+}$ concentrations in the 100 nM to 1 microM range.) At the end of 30 minutes, 45 ml of assay buffer [1×HBSS (Hank's Balanced Salt Solution), 20 mM HEPES (4-(2-Hydroxyethyl)-1-piperazineethanesulfonic acid)] was added to wash cells and the resulting mixture was then centrifuged at 850 rpm for 3 minutes to remove excess buffer and Fluo-4 AM calcium indicator. The pellet cells were re-suspended in 10 ml assay buffer and 90 ul aliquots (~50,000 cells) per well delivered to a 96-well assay plate containing 10 ul of test compounds (1 mM in assay buffer, final concentration 100 uM) or buffer control and incubated at room temperature for 30 minutes. After 30 minutes, plate is placed into a fluorometric imaging plate reader ($FLIPR^{384}$ from Molecular Devices) and basal fluorescence recorded (excitation wave length 488 nm and emission wave length 510 nm). The FLIPR assay is an accepted method for detecting changes in intracellular calcium concentration. Then 20 ul of 37.5 uM of TRPM8 agonist G-180 coolant in the assay buffer (final concentration 6.25 uM) was added and fluorescence recorded. For determining the direct effect of test compounds on TRPM8fluorescence was measured immediately after addition of each compound. Results are summarized in Table 2 below. Of the compounds tested the coolant G-180 activated the TRPM8 receptor as indicated by a significant increase in calcium ion flux vs. control. In one test, positive modulation of the G-180 activity was observed with phytic acid indicated by a 23.36% increase in calcium fluorescence for the combination compared to G-180 alone. In separate experiments using the same protocol, positive modulation was confirmed for phytic acid and demonstrated for other phosphate compounds including inorganic polyphosphate salts and an organophosphate and for polycarboxylates, such as a copolymer of maleic anhydride or acid and methyl vinyl ether (available as Gantrez®).

TABLE 2

Effect of Pre-treatment with Test Compounds on Calcium-flux in the TRPM8 Receptor As Measured by Fluorescence

| Treatment | Average Fluorescence (n = 3) | % Change from G-180 value |
|---|---|---|
| Assay buffer | 110.59 | — |
| 100 uM Carbomer 956 | 85.31 | — |
| 100 uM CMC | 40.47 | — |
| 100 uM Phytic acid | 129.38 | — |
| 100 uM Sodium lauryl sulfate | 484.55 | — |
| 6.25 uM G-180 | 14901.88 | — |
| 100 uM Phytic acid + 6.25 uM G-180 | 18382.62 | 23.36 |
| 100 uM Carbomer 956 + 6.25 uM G-180 | 13228.25 | −11.23 |
| 100 uM CMC + 6.25 uM G-180 | 8774.76 | −41.12 |
| 100 uM Sodium lauryl sulfate + 6.25 uM G-180 | 13707.57 | −8.01 |
| 6.25 uM G-180 | 17511.73 | |
| 100 uM Poly vinyl pyrrolidone + 6.25 uM G-180 | 17147.6 | −2.08 |
| 100 uM Penta sodium triphosphate + 6.25 uM G-180 | 17628.02 | 0.66 |
| 100 uM Sodium acid pyrophosphate + 6.25 uM G-180 | 18075.77 | 3.22 |
| 100 uM Sodium phosphate + 6.25 uM G-180 | 18209.98 | 3.99 |
| 100 uM Dicalcium phosphate + 6.25 uM G-180 | 18262.74 | 4.29 |

TABLE 2-continued

Effect of Pre-treatment with Test Compounds on Calcium-flux in the TRPM8 Receptor As Measured by Fluorescence

| Treatment | Average Fluorescence (n = 3) | % Change from G-180 value |
|---|---|---|
| 100 uM Sodium lauryl phosphate + 6.25 uM G-180 | 18404.83 | 5.10 |
| 100 uM Sodium tripolyphosphate + 6.25 uM G-180 | 18508.43 | 5.69 |
| 100 uM Sodium hexametaphosphate (Glass H) + 6.25 uM G-180 | 18632.54 | 6.40 |
| 100 uM Gantrez ® S-97 + 6.25 uM G-180 | 20126.81 | 14.93 |
| 6.25 uM G-180 | 17474.37 | |
| 100 uM Phytic Acid + 6.25 uM G-180 | 21178.86 | 21.20 |

Thus compositions according to the present invention comprise a calcium ion source and/or a calcium ion carrier or transport agent as potentiating agent to enhance the cooling and refreshing sensation provided by a coolant. In one embodiment, the composition comprises one or more of a calcium salt, a phytate salt or other phosphate compound or a carboxylate compound in combination with a non-menthol coolant, preferably of the menthanecarboxamide type. The composition preferably will also contain menthol which may be supplied in the composition as a single or purified chemical and/or by addition of natural oils or extracts containing menthol such as peppermint and corn mint Phytate, phosphate and carboxy compounds suitable as calcium ion carriers are described in detail below as tooth substantive and chelating agents at a level of at least about 0.1% by weight in the composition. Effective calcium ion carriers for use in the present invention are those species of tooth substantive and chelating agents that bind calcium producing soluble products that allow transport through the TRPM8 receptor.

Flavor System

The coolant(s) and optionally, menthol would typically be part of a flavor system, preferably one that effectively masks any unpleasant taste and sensations due to certain components of the composition such as antimicrobial actives or peroxide. Pleasant tasting compositions improve user compliance to prescribed or recommended use of oral care products. The present flavor system may also comprise traditional flavor components, in particular those that are relatively stable in the presence of usual oral care product carrier materials or excipients. The combination of the selected flavoring components with the coolant(s) provides a high-impact refreshing sensation with a well-rounded flavor profile.

The oral care composition will comprise from about 0.001% to 1.5% by weight of non-menthol coolant(s). If present, typically the level of menthol in the final composition ranges from about 0.010% up to about 2.0%.

In addition to the coolant(s) above, the flavor system may comprise additional flavor ingredients including but not limited to peppermint oil, corn mint oil, spearmint oil, oil of wintergreen, clove bud oil, cassia, sage, parsley oil, marjoram, lemon, lime, orange, cis-jasmone, 2,5-dimethyl-4-hydroxy-3 (2H)-furanone, 5-ethyl-3-hydroxy-4-methyl-2(5H)-furanone, vanillin, ethyl vanillin, anisaldehyde, 3,4-methylenedioxybenzaldehyde, 3,4-dimethoxybenzaldehyde, 4-hydroxybenzaldehyde, 2-methoxybenzaldehyde, benzaldehyde; cinnamaldehyde, hexyl cinnamaldehyde, alpha-methyl cinnamaldehyde, ortho-methoxy cinnamaldehyde, alpha-amyl cinnamaldehydepropenyl guaethol, heliotropine, 4-cis-heptenal, diacetyl, methyl-p-tert-butyl phenyl acetate, menthol, methyl salicylate, ethyl salicylate, 1-menthyl acetate, oxanone, alpha-irisone, methyl cinnamate, ethyl cinnamate, butyl cinnamate, ethyl butyrate, ethyl acetate, methyl anthranilate, iso-amyl acetate, iso-amyl butyrate, allyl caproate, eugenol, eucalyptol, thymol, cinnamic alcohol, octanol, octanal, decanol, decanal, phenylethyl alcohol, benzyl alcohol, alpha-terpineol, linalool, limonene, citral, maltol, ethyl maltol, anethole, dihydroanethole, carvone, menthone, β-damascenone, ionone, gamma decalactone, gamma nonalactone, gamma undecalactone and mixtures thereof. Generally suitable flavoring ingredients are those containing structural features and functional groups that are less prone to redox reactions. These include derivatives of flavor chemicals that are saturated or contain stable aromatic rings or ester groups. Also suitable are flavor chemicals that may undergo some oxidation or degradation without resulting in a significant change in the flavor character or profile. The flavor ingredients may be supplied in the composition as single or purified chemicals or by addition of natural oils or extracts that have preferably undergone a refining treatment to remove components that are relatively unstable and may degrade and alter the desired flavor profile, resulting in a less acceptable product from an organoleptic standpoint. Flavoring agents are generally used in the compositions at levels of from about 0.001% to about 5%, by weight of the composition.

The flavor system will typically include a sweetening agent. Suitable sweeteners include those well known in the art, including both natural and artificial sweeteners. Some suitable water-soluble sweeteners include monosaccharides, disaccharides and polysaccharides such as xylose, ribose, glucose (dextrose), mannose, galactose, fructose (levulose), sucrose (sugar), maltose, invert sugar (a mixture of fructose and glucose derived from sucrose), partially hydrolyzed starch, corn syrup solids, dihydrochalcones, monellin, stevioside, and glycyrrhizin. Suitable water-soluble artificial sweeteners include soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (acesulfame-K), the free acid form of saccharin, and the like. Other suitable sweeteners include dipeptide based sweeteners, such as L-aspartic acid derived sweeteners, such as L-aspartyl-L-phenylalanine methyl ester (aspartame) and materials described in U.S. Pat. No. 3,492,131 L-alpha-aspartyl-N-(2,2,4,4-tetramethyl-3-thietanyl)-D-alaninamide hydrate, methyl esters of L-aspartyl-L-phenylglycerin and L-aspartyl-L-2,5,dihydrophenyl-glycine, L-aspartyl-2,5-dihydro-L-phenylalanine, L-aspartyl-L-(1-cyclohexylen)-alanine, and the like. Water-soluble sweeteners derived from naturally occurring water-soluble sweeteners, such as a chlorinated derivative of ordinary sugar (sucrose), known, for example, under the product description of sucralose as well as protein based sweeteners such as thaumatoccous danielli (Thaumatin I and II) can be used. A composition preferably contains from about 0.1% to about 10% of sweetener, preferably from about 0.1% to about 1%, by weight of the composition.

In addition the flavor system may include salivating agents, warming agents, and numbing agents. These agents are present in the compositions at a level of from about 0.001% to about 10%, preferably from about 0.1% to about 1%, by weight of the composition. Suitable salivating agents include Jambu® manufactured by Takasago. Suitable numbing agents include benzocaine, lidocaine, clove bud oil, and ethanol. Examples of warming agents include ethanol, capsicum and nicotinate esters, such as benzyl nicotinate. Use of agents with warming effects may of course alter the cooling effect of coolants and will need to be considered, particularly in optimizing the level of coolants.

In addition to the components described above, the present compositions may comprise additional optional components collectively referred to as orally acceptable carrier materials, which are described in the following paragraphs.

Orally Acceptable Carrier Materials

The orally acceptable carrier comprises one or more compatible solid or liquid excipients or diluents which are suitable for topical oral administration. By "compatible," as used herein, is meant that the components of the composition are capable of being comingled without interaction in a manner which would substantially reduce stability and/or efficacy.

The carriers or excipients of the present invention can include the usual and conventional components of dentifrices, non-abrasive gels, subgingival gels, mouthwashes or rinses, mouth sprays, chewing gums, lozenges and breath mints as more fully described hereinafter.

The choice of a carrier to be used is basically determined by the way the composition is to be introduced into the oral cavity. Carrier materials for toothpaste, tooth gel or the like include abrasive materials, sudsing agents, binders, humectants, flavoring and sweetening agents, etc. as disclosed in e.g., U.S. Pat. No. 3,988,433 to Benedict. Carrier materials for biphasic dentifrice formulations are disclosed in U.S. Pat. Nos. 5,213,790; 5,145,666 and 5,281,410 all to Lukacovic et al. and in U.S. Pat. Nos. 4,849,213 and 4,528,180 to Schaeffer. Mouthwash, rinse or mouth spray carrier materials typically include water, flavoring and sweetening agents, etc., as disclosed in, e.g., U.S. Pat. No. 3,988,433 to Benedict. Lozenge carrier materials typically include a candy base; chewing gum carrier materials include a gum base, flavoring and sweetening agents, as in, e.g., U.S. Pat. No. 4,083,955 to Grabenstetter et al. Sachet carrier materials typically include a sachet bag, flavoring and sweetening agents. For subgingival gels used for delivery of actives into the periodontal pockets or around the periodontal pockets, a "subgingival gel carrier" is chosen as disclosed in, e.g. U.S. Pat. Nos. 5,198,220 and 5,242,910 both to Damani. Carriers suitable for the preparation of compositions of the present invention are well known in the art. Their selection will depend on secondary considerations like taste, cost, and shelf stability, etc.

The compositions of the present invention may also be in the form of non-abrasive gels and subgingival gels, which may be aqueous or non-aqueous. In still another aspect, the invention provides a dental implement impregnated with the present composition. The dental implement comprises an implement for contact with teeth and other tissues in the oral cavity, said implement being impregnated with the present composition. The dental implement can be impregnated fibers including dental floss or tape, chips, strips, films and polymer fibers.

In one embodiment, the compositions of the subject invention are in the form of dentifrices, such as toothpastes, tooth gels and tooth powders. Components of such toothpaste and tooth gels generally include one or more of a dental abrasive (from about 6% to about 50%), a surfactant (from about 0.5% to about 10%), a thickening agent (from about 0.1% to about 5%), a humectant (from about 10% to about 55%), a flavoring agent (from about 0.04% to about 2%), a sweetening agent (from about 0.1% to about 3%), a coloring agent (from about 0.01% to about 0.5%) and water (from about 2% to about 45%). Such toothpaste or tooth gel may also include one or more of an anticaries agent (from about 0.05% to about 0.3% as fluoride ion) and an anticalculus agent (from about 0.1% to about 13%). Tooth powders, of course, contain substantially all non-liquid components.

Other embodiments of the subject invention are liquid products, including mouthwashes or rinses, mouth sprays, dental solutions and irrigation fluids. Components of such mouthwashes and mouth sprays typically include one or more of water (from about 45% to about 95%), ethanol (from about 0% to about 25%), a humectant (from about 0% to about 50%), a surfactant (from about 0.01% to about 7%), a flavoring agent (from about 0.04% to about 2%), a sweetening agent (from about 0.1% to about 3%), and a coloring agent (from about 0.001% to about 0.5%). Such mouthwashes and mouth sprays may also include one or more of an anticaries agent (from about 0.05% to about 0.3% as fluoride ion) and an anticalculus agent (from about 0.1% to about 3%). Components of dental solutions generally include one or more of water (from about 90% to about 99%), preservative (from about 0.01% to about 0.5%), thickening agent (from 0% to about 5%), flavoring agent (from about 0.04% to about 2%), sweetening agent (from about 0.1% to about 3%), and surfactant (from 0% to about 5%).

Types of orally acceptable carriers or excipients which may be included in compositions of the present invention, along with specific non-limiting examples, are discussed in the following paragraphs.

Fluoride Source

It is common to have a water-soluble fluoride compound present in dentifrices and other oral compositions in an amount sufficient to give a fluoride ion concentration in the composition, and/or when it is used of from about 0.0025% to about 5.0% by weight, preferably from about 0.005% to about 2.0% by weight, to provide anticaries effectiveness. A wide variety of fluoride ion-yielding materials can be employed as sources of soluble fluoride in the present compositions. Examples of suitable fluoride ion-yielding materials are found in U.S. Pat. No. 3,535,421 to Briner et al. and U.S. Pat. No. 3,678,154 to Widder et al. Representative fluoride ion sources include: stannous fluoride, sodium fluoride, potassium fluoride, sodium monofluorophosphate, indium fluoride, amine fluoride and many others.

Abrasives

Dental abrasives useful in the compositions of the subject invention include many different materials. The material selected must be one which is compatible within the composition of interest and does not excessively abrade dentin. Suitable abrasives include, for example, silicas including gels and precipitates, insoluble sodium polymetaphosphate, hydrated alumina, calcium carbonate, dicalcium orthophosphate dihydrate, calcium pyrophosphate, tricalcium phosphate, calcium polymetaphosphate, and resinous abrasive materials such as particulate condensation products of urea and formaldehyde.

Another class of abrasives for use in the present compositions is the particulate thermo-setting polymerized resins as described in U.S. Pat. No. 3,070,510 issued to Cooley & Grabenstetter. Suitable resins include, for example, melamines, phenolics, ureas, melamine-ureas, melamine-formaldehydes, urea-formaldehyde, melamine-urea-formaldehydes, cross-linked epoxides, and cross-linked polyesters.

Silica dental abrasives of various types are preferred because of their unique benefits of exceptional dental cleaning and polishing performance without unduly abrading tooth enamel or dentine. The silica abrasive polishing materials herein, as well as other abrasives, generally have an average particle size ranging between about 0.1 to about 30 microns, and preferably from about 5 to about 15 microns. The abrasive can be precipitated silica or silica gels such as the silica xerogels described in Pader et al., U.S. Pat. No. 3,538,230 and DiGiulio, U.S. Pat. No. 3,862,307Examples include the silica xerogels marketed under the trade name "Syloid" by the W.R. Grace & Company, Davison Chemical Division and precipitated silica materials such as those marketed by the J. M. Huber Corporation under the trade name, Zeodent®particularly the silicas carrying the designation Zeodent® 119Zeodent® 118Zeodent® 109 and Zeodent® 129The types of silica dental abrasives useful in the toothpastes of the present invention are described in more detail in Wason, U.S. Pat. No. 4,340,583issued Jul. 29, 1982and in commonly-assigned U.S. Pat. Nos. 5,603,920; 5,589,160; 5,658,553; 5,651,958 and 6,740,311.

Mixtures of abrasives can be used such as mixtures of the various grades of Zeodent® silica abrasives listed above. The total amount of abrasive in dentifrice compositions of the subject invention typically range from about 6% to about 70% by weight; toothpastes preferably contain from about 10% to about 50% of abrasives, by weight of the composition. Dental solution, mouth spray, mouthwash and non-abrasive gel compositions of the subject invention typically contain little or no abrasive.

Peroxide Source

The present compositions may optionally contain a peroxide source for its many benefits to the oral cavity. It has long been recognized that hydrogen peroxide and other peroxygen-containing agents are effective in curative and/or prophylactic treatments with respect to caries, dental plaque, gingivitis, periodontitis, mouth odor, tooth stains, recurrent aphthous ulcers, denture irritations, orthodontic appliance lesions, postextraction and postperiodontal surgery, traumatic oral lesions and mucosal infections, herpetic stomatitis and the like. Peroxide-containing agents in the oral cavity exert a chemomechanical action generating thousands of tiny oxygen bubbles produced by interaction with tissue and salivary enzymes. The swishing action of a mouthrinse enhances this inherent chemomechanical action. Such action has been recommended for delivery of other agents into infected gingival crevices. Peroxide mouthrinses prevent colonization and multiplication of anaerobic bacteria known to be associated with periodontal disease. However, compositions containing hydrogen peroxide or other peroxide releasing compounds generally provide disagreeable taste and mouth sensations. These sensations have been described as stinging, prickling and irritating, similar to that experienced when the tongue comes into contact with sharp flavors or highly carbonated liquids such as club soda. In addition peroxides interact with other common excipients therein and tend to be unstable in storage, continuously losing the capacity to release active or nascent oxygen over relatively short periods of time, and tend to diminish or destroy the desired function of such excipients. Among such excipients are flavors, sensory materials and coloring agents added to enhance the acceptability of the oral care product.

Peroxide sources include peroxide compounds, perborates, percarbonates, peroxyacids, persulfates, and combinations thereof. Suitable peroxide compounds include hydrogen peroxide, urea peroxide, calcium peroxide, sodium peroxide, zinc peroxide and mixtures thereof. A preferred percarbonate is sodium percarbonate. Preferred persulfates are oxones. Preferred peroxide sources for use in dentifrice formulations include calcium peroxide and urea peroxide. Hydrogen peroxide and urea peroxide are preferred for use in mouthrinse formulations. The following amounts represent the amount of peroxide raw material, although the peroxide source may contain ingredients other than the peroxide raw material. The present composition may contain from about 0.01% to about 30%, preferably from about 0.1% to about 10%, and more preferably from about 0.5% to about 5% of a peroxide source, by weight of the composition.

Anticalculus Agent

The present compositions may optionally include an anticalculus agent, such as a pyrophosphate salt as a source of pyrophosphate ion, which has chelating activity. Chelating agents are known in the art to retard calculus formation and to remove calculus after it is formed. The chemical approach to calculus inhibition generally involves chelation of calcium ion and/or crystal growth inhibition which prevents the calculus from forming and/or breaks down mature calculus by removing calcium. In addition, chelating agents can in principle remove stains by binding to teeth surfaces thereby displacing color bodies or chromagens. The pyrophosphate salts useful in the present compositions include the dialkali metal pyrophosphate salts, tetraalkali metal pyrophosphate salts, and mixtures thereof. Disodium dihydrogen pyrophosphate ($Na_2H_2P_2O_7$), tetrasodium pyrophosphate ($Na_4P_2O_7$), and tetrapotassium pyrophosphate ($K_4O_2O_7$) in their unhydrated as well as hydrated forms are the preferred species. In compositions of the present invention, the pyrophosphate salt may be present in one of three ways: predominately dissolved, predominately undissolved, or a mixture of dissolved and undissolved pyrophosphate.

Compositions comprising predominately dissolved pyrophosphate refer to compositions where at least one pyrophosphate ion source is in an amount sufficient to provide at least about 1.0% free pyrophosphate ions. The amount of free pyrophosphate ions may be from about 1% to about 15%, from about 1.5% to about 10% in one embodiment, and from about 2% to about 6% in another embodiment. Free pyrophosphate ions may be present in a variety of protonated states depending on the pH of the composition.

Compositions comprising predominately undissolved pyrophosphate refer to compositions containing no more than about 20% of the total pyrophosphate salt dissolved in the composition, preferably less than about 10% of the total pyrophosphate dissolved in the composition. Tetrasodium pyrophosphate salt is a preferred pyrophosphate salt in these compositions. Tetrasodium pyrophosphate may be the anhydrous salt form or the decahydrate form, or any other species stable in solid form in the dentifrice compositions. The salt is in its solid particle form, which may be its crystalline and/or amorphous state, with the particle size of the salt preferably being small enough to be aesthetically acceptable and readily soluble during use. The amount of pyrophosphate salt useful in making these compositions is any tartar control effective amount, generally from about 1.5% to about 15%, preferably from about 2% to about 10%, and most preferably from about 3% to about 8%, by weight of the dentifrice composition.

Compositions may also comprise a mixture of dissolved and undissolved pyrophosphate salts. Any of the above mentioned pyrophosphate salts may be used.

The pyrophosphate salts are described in more detail in *Kirk-Othmer Encyclopedia of Chemical Technology* Third Edition, Volume 17 Wiley-Interscience Publishers (1982).

Optional agents to be used in place of or in combination with the pyrophosphate salt include such known materials as synthetic anionic polymers, including polyacrylates and copolymers of maleic anhydride or acid and methyl vinyl ether (e.g., Gantrez), as described, for example, in U.S. Pat. No. 4,627,977 to Gaffar et al., as well as, e.g., polyamino propane sulfonic acid (AMPS), diphosphonates (e.g., EHDP; AHP), polypeptides (such as polyaspartic and polyglutamic acids), and mixtures thereof.

Tooth Substantive Agent

The present invention may include a tooth substantive agent such as polymeric surface active agents (PMSA's), which are polyelectrolytes, more specifically anionic polymers. The PMSA's contain anionic groups, e.g., phosphate, phosphonate, carboxy, or mixtures thereof, and thus, have the capability to interact with cationic or positively charged entities. The "mineral" descriptor is intended to convey that the surface activity or substantivity of the polymer is toward mineral surfaces such as calcium phosphate minerals or teeth.

PMSA's are useful in the present compositions because of their many benefits such as stain prevention. It is believed the PMSA's provide a stain prevention benefit because of their reactivity or substantivity to mineral or tooth surfaces, resulting in desorption of portions of undesirable adsorbed pellicle proteins, in particular those associated with binding color bodies that stain teeth, calculus development and attraction of undesirable microbial species. The retention of these PMSA's on teeth can also prevent stains from accruing due to disruption of binding sites of color bodies on tooth surfaces.

The ability of PMSA's to bind stain promoting ingredients of oral care products such as stannous ions and cationic antimicrobials is also believed to be helpful. The PMSA will also provide tooth surface conditioning effects which produce desirable effects on surface thermodynamic properties and surface film properties, which impart improved clean feel aesthetics both during and most importantly, following rinsing or brushing. Many of these agents are also expected to provide tartar control benefits when included in oral compositions, hence providing improvement in both the appearance of teeth and their tactile impression to consumers.

The desired surface effects may include: 1) creating a hydrophilic tooth surface immediately after treatment; and 2) maintaining surface conditioning effects and control of pellicle film for extended periods following product use, including post brushing or rinsing and throughout more extended periods. The effect of creating an increased hydrophilic surface can be measured in terms of a relative decrease in water contact angles. The hydrophilic surface, importantly, is maintained on the tooth surface for an extended period after using the product.

The PMSA's include any agent which will have a strong affinity for the tooth surface, deposit a polymer layer or coating on the tooth surface and produce the desired surface modification effects. Suitable examples of such polymers are polyelectrolytes such as condensed phosphorylated polymers; polyphosphonates; copolymers of phosphate- or phosphonate-containing monomers or polymers with other monomers such as ethylenically unsaturated monomers and amino acids or with other polymers such as proteins, polypeptides, polysaccharides, poly(acrylate), poly(acrylamide), poly(methacrylate), poly(ethacrylate), poly(hydroxyalkylmethacrylate), poly(vinyl alcohol), poly(maleic anhydride), poly(maleate) poly(amide), poly(ethylene amine), poly(ethylene glycol), poly(propylene glycol), poly(vinyl acetate) and poly(vinyl benzyl chloride); polycarboxylates and carboxy-substituted polymers; and mixtures thereof. Suitable polymeric mineral surface active agents include the carboxy-substituted alcohol polymers described in U.S. Pat. Nos. 5,292,501; 5,213,789, 5,093,170; 5,009,882 and 4,939,284 all to Degenhardt et al. and the diphosphonate-derivatized polymers in U.S. Pat. No. 5,011,913 to Benedict et al; the synthetic anionic polymers including polyacrylates and copolymers of maleic anhydride or acid and methyl vinyl ether (e.g., Gantrez), as described, for example, in U.S. Pat. No. 4,627,977 to Gaffar et al. A preferred polymer is diphosphonate modified polyacrylic acid. Polymers with activity must have sufficient surface binding propensity to desorb pellicle proteins and remain affixed to enamel surfaces. For tooth surfaces, polymers with end or side chain phosphate or phosphonate functions are preferred although other polymers with mineral binding activity may prove effective depending upon adsorption affinity.

Additional examples of suitable phosphonate containing polymeric mineral surface active agents include the geminal diphosphonate polymers disclosed as anticalculus agents in U.S. Pat. No. 4,877,603 to Degenhardt et al; phosphonate group containing copolymers disclosed in U.S. Pat. No. 4,749,758 to Dursch et al. and in GB 1,290,724 (both assigned to Hoechst) suitable for use in detergent and cleaning compositions; and the copolymers and cotelomers disclosed as useful for applications including scale and corrosion inhibition, coatings, cements and ion-exchange resins in U.S. Pat. No. 5,980,776 to Zakikhani et al. and U.S. Pat. No. 6,071,434 to Davis et al. Additional polymers include the water-soluble copolymers of vinylphosphonic acid and acrylic acid and salts thereof disclosed in GB 1,290,724 wherein the copolymers contain from about 10% to about 90% by weight vinylphosphonic acid and from about 90% to about 10% by weight acrylic acid, more particularly wherein the copolymers have a weight ratio of vinylphosphonic acid to acrylic acid of 70% vinylphosphonic acid to 30% acrylic acid; 50% vinylphosphonic acid to 50% acrylic acid; or 30% vinylphosphonic acid to 70% acrylic acid. Other suitable polymers include the water soluble polymers disclosed by Zakikhani and Davis prepared by copolymerizing diphosphonate or polyphosphonate monomers having one or more unsaturated C=C bonds (e.g., vinylidene-1,1-diphosphonic acid and 2-(hydroxyphosphinyl)ethylidene-1,1-diphosphonic acid), with at least one further compound having unsaturated C=C bonds (e.g., acrylate and methacrylate monomers), such as those having the following structure:

1 Co-telomer of acrylic acid and 2-(hydroxyphosphinyl)ethylidene-1,1-diphosphonic acid with structure:

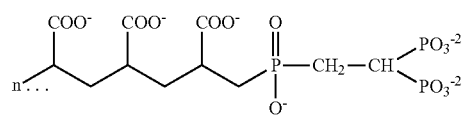

2 Co-polymer of acrylic acid and vinyldiphosphonic acid with structure:

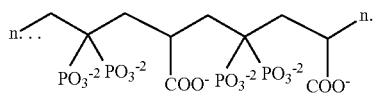

Suitable polymers include the diphosphonate/acrylate polymers supplied by Rhodia under the designation ITC 1087 (Average MW 3000-60,000) and Polymer 1154 (Average MW 6000-55,000).

A preferred PMSA will be stable with other components of the oral care composition such as ionic fluoride and metal ions. Also preferred are polymers that have limited hydrolysis in high water content formulations, thus permitting a simple single phase dentifrice or mouthrinse formulation. If the PMSA does not have these stability properties, one option is a dual phase formulation with the polymeric mineral surface active agent separated from the fluoride or other incompatible component. Another option is to formulate non-aqueous, essentially non-aqueous or limited water compositions to minimize reaction between the PMSA and other components.

One preferred PMSA is a polyphosphate. A polyphosphate is generally understood to consist of two or more phosphate molecules arranged primarily in a linear configuration, although some cyclic derivatives may be present. Although pyrophosphates (n=2) are technically polyphosphates, the polyphosphates desired are those having around three or more phosphate groups so that surface adsorption at effective concentrations produces sufficient non-bound phosphate functions, which enhance the anionic surface charge as well as hydrophilic character of the surfaces. The inorganic polyphosphate salts desired include tripolyphosphate, tetrapolyphosphate and hexametaphosphate, among others. Polyphosphates larger than tetrapolyphosphate usually occur as amorphous glassy materials. Preferred in the present compositions are the linear polyphosphates having the formula: $XO(XPO_3)_nX$, wherein X is sodium, potassium or ammonium and n averages from about 3 to about 125 Preferred polyphosphates are those having n averaging from about 6 to about 21 such as those commercially known as Sodaphos (n≈6), Hexaphos (n≈13), and Glass H (n≈21) and manufactured by FMC Corporation and Astaris. These polyphosphates may be used alone or in combination. Polyphosphates are susceptible to hydrolysis in high water formulations at acid pH, particularly below pH 5 Thus it is preferred to use longer-chain polyphosphates, in particular Glass H with an average chain length of about 21 It is believed such longer-chain polyphosphates when undergoing hydrolysis produce shorter-chain polyphosphates which are still effective to deposit onto teeth and provide a stain preventive benefit.

Other polyphosphorylated compounds may be used in addition to or instead of the polyphosphate, in particular polyphosphorylated inositol compounds such as phytic acid, myo-inositol pentakis(dihydrogen phosphate); myo-inositol tetrakis(dihydrogen phosphate), myo-inositol trikis(dihydrogen phosphate), and an alkali metal, alkaline earth metal or ammonium salt thereof. Preferred herein is phytic acid, also known as myo-inositol 1,2,3,4,5,6-hexakis (dihydrogen phosphate) or inositol hexaphosphoric acid, and its alkali metal, alkaline earth metal or ammonium salts. Herein, the term "phytate" includes phytic acid and its salts as well as the other polyphosphorylated inositol compounds.

Still other surface active organophosphate compounds useful as tooth substantive agents include phosphate mono-, di- or triesters represented by the following general structure

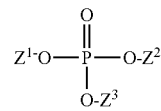

wherein $Z^1 Z^2$ or $Z^3$ may be identical or different, at least one being an organic moiety, preferably selected from linear or branched, alkyl or alkenyl group of from 6 to 22 carbon atoms, optionally substituted by one or more phosphate groups; alkoxylated alkyl or alkenyl, (poly)saccharide, polyol or polyether group.

Some preferred agents include alkyl or alkenyl phosphate esters represented by the following structure:

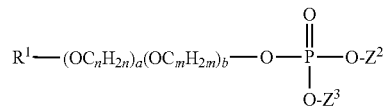

wherein $R^1$ represents a linear or branched, alkyl or alkenyl group of from 6 to 22 carbon atoms, optionally substituted by one or more phosphate groups; n and m, are individually and separately, 2 to 4 and a and b, individually and separately, are 0 to 20 $Z^2$ and $Z^3$ may be identical or different, each represents hydrogen, alkali metal, ammonium, protonated alkyl amine or protonated functional alkyl amine such as an alkanolamine, or a $R^1$—$(OC_nH_{2n})_a(OC_mH_{2m})_b$— group. Examples of preferred agents include mono- di- and tri-alkyl and alkyl (poly)alkoxy phosphates such as dodecyl phosphate, lauryl phosphate; laureth-1 phosphate; laureth-3 phosphate; laureth-9 phosphate; dilaureth-10 phosphate; trilaureth-4 phosphate; C12-18 PEG-9 phosphate and salts thereof. Many are commercially available from suppliers including Croda; Rhodia; Nikkol Chemical; Sunjin; Alzo; Huntsman Chemical; Clariant and Cognis. Some preferred agents are polymeric, for example those containing repeating alkoxy groups as the polymeric portion, in particular 3 or more ethoxy, propoxy isopropoxy or butoxy groups.

Additional suitable polymeric organophosphate agents include dextran phosphate, polyglucoside phosphate, alkyl polyglucoside phosphate, polyglyceryl phosphate, alkyl polyglyceryl phosphate, polyether phosphates and alkoxylated polyol phosphates. Some specific examples are PEG phosphate, PPG phosphate, alkyl PPG phosphate, PEG/PPG phosphate, alkyl PEG/PPG phosphate, PEG/PPG/PEG phosphate, dipropylene glycol phosphate, PEG glyceryl phosphate, PBG (polybutylene glycol) phosphate, PEG cyclodextrin phosphate, PEG sorbitan phosphate, PEG alkyl sorbitan phosphate, and PEG methyl glucoside phosphate.

Additional suitable non-polymeric phosphates include alkyl mono glyceride phosphate, alkyl sorbitan phosphate, alkyl methyl glucoside phosphate, alkyl sucrose phosphates.

The amount of tooth substantive agent will typically be from about 0.1% to about 35% by weight of the total oral composition. In dentifrice formulations, the amount is preferably from about 2% to about 30%, more preferably from about 5% to about 25%, and most preferably from about 6% to about 20%. In mouthrinse compositions, the amount of tooth substantive agent is preferably from about 0.1% to 5% and more preferably from about 0.5% to about 3%.

In addition to creating surface modifying effects, the tooth substantive agent may also function to solubilize insoluble salts. For example, Glass H has been found to solubilize insoluble stannous salts. Thus, in compositions containing stannous fluoride for example, Glass H contributes to decreasing the staining due to stannous.

Chelating Agents

The present compositions may optionally contain chelating agents, also called sequestrants, many of which also have anticalculus activity. Use of chelating agents in oral care products is advantageous for their ability to complex calcium such as found in the cell walls of bacteria. Chelating agents can also disrupt plaque by removing calcium from the calcium bridges which help hold this biomass intact. However, it is not desired to use a chelating agent which has an affinity for calcium that is too high, as this may result in tooth demineralization, which is contrary to the objects and intentions of the present invention. Suitable chelating agents will generally have a calcium binding constant of about $10^1$ to $10^5$ to provide improved cleaning with reduced plaque and calculus formation. Chelating agents also have the ability to complex with metallic ions and thus aid in preventing their adverse effects on the stability or appearance of products. Chelation of ions, such as iron or copper, helps retard oxidative deterioration of finished products.

Because chelating agents will bind calcium, their presence in the composition may affect the availability of calcium ions to provide the coolant potentiating effect. The level of the calcium source in the composition may therefore need to be adjusted depending on the chelating agent used. The ideal chelating agent for the present compositions would be agents that have calcium binding ability and also function as calcium solubilizing and transport agent through receptor ion channels. Such agents include soluble phosphate compounds, such as phytates and linear polyphosphates having three or more phosphate groups such as described above, including tripolyphosphate, tetrapolyphosphate and hexametaphosphate, among others. Preferred polyphosphates are those having the number of phosphate groups n averaging from about 6 to about 21 such as those commercially known as Sodaphos (n≈6), Hexaphos (n≈13), and Glass H (n≈21). The amount of chelating agent in the compositions will depend on the chelating agent used and typically will be from at least about 0.1% to about 20%, preferably from about 0.5% to about 10% and more preferably from about 1.0% to about 7%.

Still other phosphate compounds that are useful herein for their ability to bind, solubilize and transport calcium are the surface active organophosphate compounds described above useful as tooth substantive agents including organic phosphate mono-, di- or triesters.

Other examples of chelating agents are sodium or potassium gluconate and citrate; citric acid/alkali metal citrate combination; disodium tartrate; dipotassium tartrate; sodium potassium tartrate; sodium hydrogen tartrate; potassium hydrogen tartrate; and mixtures thereof.

Still other chelating agents suitable for use in the present invention are the anionic polymeric polycarboxylates. Such materials are well known in the art, being employed in the form of their free acids or partially or preferably fully neutralized water soluble alkali metal (e.g. potassium and preferably sodium) or ammonium salts. Examples are 1:4 to 4:1 copolymers of maleic anhydride or acid with another polymerizable ethylenically unsaturated monomer, preferably methyl vinyl ether (methoxyethylene) having a molecular weight (M.W.) of about 30,000 to about 1,000,000 These copolymers are available for example as Gantrez® AN 139 (M.W. 500,000), AN 119 (M.W. 250,000) and S-97 Pharmaceutical Grade (M.W. 70,000), of GAF Chemicals Corporation.

Other operative polymeric polycarboxylates include the 1:1 copolymers of maleic anhydride with ethyl acrylate, hydroxyethyl methacrylate, N-vinyl-2-pyrrolidone, or ethylene, the latter being available for example as Monsanto EMA No. 1103 M.W. 10,000 and EMA Grade 61 and 1:1 copolymers of acrylic acid with methyl or hydroxyethyl methacrylate, methyl or ethyl acrylate, isobutyl vinyl ether or N-vinyl-2-pyrrolidone.

Additional operative polymeric polycarboxylates are disclosed in U.S. Pat. No. 4,138,477 Feb. 6, 1979 to Gaffar and U.S. Pat. No. 4,183,914 Jan. 15, 1980 to Gaffar et al. and include copolymers of maleic anhydride with styrene, isobutylene or ethyl vinyl ether; polyacrylic, polyitaconic and polymaleic acids; and sulfoacrylic oligomers of M.W. as low as 1,000 available as Uniroyal ND-2.

Other Active Agents

The present compositions may optionally include other active agents, such as antimicrobial agents. Included among such agents are water insoluble non-cationic antimicrobials such as halogenated diphenyl ethers, phenolic compounds including phenol and its homologs, mono and poly-alkyl and aromatic halophenols, resorcinol and its derivatives, bisphenolic compounds and halogenated salicylanilides, benzoic esters, and halogenated carbanilides. Water soluble antimicrobials include quaternary ammonium salts and bis-biquanide salts, and triclosan monophosphate. The quaternary ammonium agents include those in which one or two of the substitutes on the quaternary nitrogen has a carbon chain length (typically alkyl group) from about 8 to about 20 typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl) ammonium bromide, benzyl dimethylstearyl ammonium chloride, cetyl pyridinium chloride, quaternized 5-amino-1, 3-bis(2-ethyl-hexyl)-5-methyl hexa hydropyrimidine, benzalkonium chloride, benzethonium chloride and methyl benzethonium chloride are exemplary of typical quaternary ammonium antibacterial agents. Other compounds are bis [4-(R-amino)-1-pyridinium]alkanes as disclosed in U.S. Pat. No. 4,206,215 to Bailey. Other antimicrobials such as copper salts, zinc salts and stannous salts may also be included. Also useful are enzymes, including endoglycosidase, papain, dextranase, mutanase, and mixtures thereof. Such agents are disclosed in U.S. Pat. No. 2,946,725 to Norris et al. and in U.S. Pat. No. 4,051,234 to Gieske et al. Preferred antimicrobial agents include zinc salts, stannous salts, cetyl pyridinium chloride, chlorhexidine, triclosan, triclosan monophosphate, and flavor oils such as thymol. Triclosan and other agents of this type are disclosed in Parran, Jr. et al., U.S. Pat. Nos. 5,015,466 and 4,894,220 to Nabi et al. These agents provide anti-plaque benefits and are typically present at levels of from about 0.01% to about 5.0%, by weight of the composition.

Another optional active agent that may be added to the present compositions are dentinal desensitizing agents to control hypersensitivity, such as salts of potassium, calcium, strontium and tin including nitrate, chloride, fluoride, phosphates, pyrophosphate, polyphosphate, citrate, oxalate and sulfate.

Surfactants

The present compositions may also comprise surfactants, also commonly referred to as sudsing agents. Suitable surfactants are those which are reasonably stable and foam throughout a wide pH range. The surfactant may be anionic, nonionic, amphoteric, zwitterionic, cationic, or mixtures thereof.

Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate (SLS) and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. Many suitable anionic surfactants are disclosed by Agricola et al., U.S. Pat. No. 3,959,458The present composition typically comprises an anionic surfactant at a level of from about 0.025% to about 9%, from about 0.05% to about 5% in some embodiments, and from about 0.1% to about 1% in other embodiments.

Another suitable surfactant is one selected from the group consisting of sarcosinate surfactants, isethionate surfactants and taurate surfactants. Preferred for use herein are alkali metal or ammonium salts of these surfactants, such as the sodium and potassium salts of the following: lauroyl sarcosinate, myristoyl sarcosinate, palmitoyl sarcosinate, stearoyl sarcosinate and oleoyl sarcosinate. The sarcosinate surfactant may be present in the compositions of the present invention from about 0.1% to about 2.5%, preferably from about 0.5% to about 2.0% by weight of the total composition.

Cationic surfactants useful in the present invention include derivatives of aliphatic quaternary ammonium compounds having one long alkyl chain containing from about 8 to 18 carbon atoms such as lauryl trimethylammonium chloride; cetyl pyridinium chloride; cetyl trimethylammonium bromide; di-isobutylphenoxyethyl-dimethylbenzylammonium chloride; coconut alkyltrimethylammonium nitrite; cetyl pyridinium fluoride; etc. Preferred compounds are the quaternary ammonium fluorides described in U.S. Pat. No. 3,535,421 to Briner et al., where said quaternary ammonium fluorides have detergent properties. Certain cationic surfactants can also act as germicides in the compositions disclosed herein. Cationic surfactants such as chlorhexidine, although suitable for use in the current invention, are not preferred due to their capacity to stain the oral cavity's hard tissues. Persons skilled in the art are aware of this possibility and should incorporate cationic surfactants with this limitation in mind.

Nonionic surfactants that can be used in the compositions of the present invention include compounds produced by the condensation of alkylene oxide groups (hydrophilic in nature) with an organic hydrophobic compound which may be aliphatic or alkylaromatic in nature. Examples of suitable nonionic surfactants include the Pluronics, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides and mixtures of such materials.

Zwitterionic or amphoteric surfactants useful in the present invention include derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate or phosphonate. Suitable amphoteric surfactants include betaine surfactants such as disclosed in U.S. Pat. No. 5,180,577 to Polefka et al. Typical alkyl dimethyl betaines include decyl betaine or 2-(N-decyl-N,N-dimethylammonio) acetate, coco betaine or 2-(N-coco-N,N-dimethyl ammonio) acetate, myristyl betaine, palmityl betaine, lauryl betaine, cetyl betaine, cetyl betaine, stearyl betaine, etc. Examples of amidobetaines are cocoamidoethyl betaine, cocamidopropyl betaine (CAPB), and lauramidopropyl betaine.

Thickening Agents

In preparing toothpaste or gels, thickening agents are added to provide a desirable consistency to the composition, to provide desirable active release characteristics upon use, to provide shelf stability, and to provide stability of the composition, etc. Suitable thickening agents include one or a combination of carboxyvinyl polymers, carrageenan, hydroxyethyl cellulose (HEC), natural and synthetic clays (e.g., Veegum and laponite) and water soluble salts of cellulose ethers such as sodium carboxymethylcellulose (CMC) and sodium carboxymethyl hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture.

Suitable carboxyvinyl polymers useful as thickening or gelling agents include carbomers which are homopolymers of acrylic acid crosslinked with an alkyl ether of pentaerythritol or an alkyl ether of sucrose. Carbomers are commercially available from B.F. Goodrich as the Carbopol® series, including Carbopol 934, 940, 941, 956and mixtures thereof.

Thickening agents are typically present in an amount from about 0.1% to about 15%, preferably from about 2% to about 10%, more preferably from about 4% to about 8%, by weight of the total toothpaste or gel composition, can be used. Higher concentrations may be used for chewing gums, lozenges and breath mints, sachets, non-abrasive gels and subgingival gels.

Humectants

Another optional carrier material of the present compositions is a humectant. The humectant serves to keep toothpaste compositions from hardening upon exposure to air, to give compositions a moist feel to the mouth, and, for particular humectants, to impart desirable sweetness of flavor to toothpaste compositions. The humectant, on a pure humectant basis, generally comprises from about 0% to about 70%, preferably from about 5% to about 25%, by weight of the compositions herein. Suitable humectants for use in compositions of the subject invention include edible polyhydric alcohols such as glycerin, sorbitol, xylitol, butylene glycol, polyethylene glycol, propylene glycol and trimethyl glycine.

Miscellaneous Carrier Materials

Water employed in the preparation of commercially suitable oral compositions should preferably be of low ion content and free of organic impurities. Water may comprise up to about 99% by weight of the aqueous compositions herein. These amounts of water include the free water which is added plus that which is introduced with other materials, such as with sorbitol.

The present invention may also include an alkali metal bicarbonate salt, which may serve a number of functions including abrasive, deodorant, buffering and adjusting pH. Alkali metal bicarbonate salts are soluble in water and unless stabilized, tend to release carbon dioxide in an aqueous system. Sodium bicarbonate, also known as baking soda, is a commonly used alkali metal bicarbonate salt. The present composition may contain from about 0.5% to about 30%, preferably from about 0.5% to about 15%, and most preferably from about 0.5% to about 5% of an alkali metal bicarbonate salt.

The pH of the present compositions may be adjusted through the use of buffering agents. Buffering agents, as used herein, refer to agents that can be used to adjust the pH of aqueous compositions such as mouthrinses and dental solutions preferably to a range of about pH 4.0 to about pH 8.0Buffering agents include sodium bicarbonate, monosodium phosphate, trisodium phosphate, sodium hydroxide, sodium carbonate, sodium acid pyrophosphate, citric acid, and sodium citrate. Buffering agents are typically included at a level of from about 0.5% to about 10%, by weight of the present compositions.

Poloxamers may be employed in the present compositions. A poloxamer is classified as a nonionic surfactant and may also function as an emulsifying agent, binder, stabilizer, and other related functions. Poloxamers are difunctional block-polymers terminating in primary hydroxyl groups with molecular weights ranging from 1,000 to above 15,000Poloxamers are sold under the tradename of Pluronics and Pluraflo by BASF. Suitable poloxamers for this invention are Poloxamer 407 and Pluraflo L4370.

Other emulsifying agents that may be used in the present compositions include polymeric emulsifiers such as the Pemulen® series available from B.F. Goodrich, and which are predominantly high molecular weight polyacrylic acid polymers useful as emulsifiers for hydrophobic substances.

Titanium dioxide may also be added to the present composition. Titanium dioxide is a white powder which adds opacity to the compositions. Titanium dioxide generally comprises from about 0.25% to about 5% by weight of dentifrice compositions.

Other optional agents that may be used in the present compositions include dimethicone copolyols selected from alkyl- and alkoxy-dimethicone copolyols, such as C12 to C20 alkyl dimethicone copolyols and mixtures thereof, which aid in providing positive tooth feel benefits. Highly preferred is cetyl dimethicone copolyol marketed under the trade name Abil EM90The dimethicone copolyol may be present at a level of from about 0.01% to about 25%, preferably from about 0.1% to about 5%, more preferably from about 0.5% to about 1.5% by weight.

Method of Use

The method of use herein comprises contacting a subject's dental enamel surfaces and mucosa with the oral compositions according to the present invention. The method of treatment may be by brushing with a dentifrice or rinsing with a dentifrice slurry or mouthrinse. Other methods include contacting the topical oral gel, denture product, mouthspray, or other form with the subject's teeth and oral mucosa. The subject may be any person or animal whose oral cavity is contacted with the oral composition. By animal is meant to include household pets or other domestic animals, or animals kept in captivity.

For example, a method of treatment may include a person brushing a dog's teeth with one of the dentifrice compositions. Another example would include the rinsing of a cat's mouth with an oral composition for a sufficient amount of time to see a benefit. Pet care products such as chews and toys may be formulated to contain the present oral compositions. The composition may be incorporated into a relatively supple but strong and durable material such as rawhide, ropes made from natural or synthetic fibers, and polymeric articles made from nylon, polyester or thermoplastic polyurethane. As the animal chews, licks or gnaws the product, the incorporated active elements are released into the animal's oral cavity into a salivary medium, comparable to an effective brushing or rinsing.

In one embodiment of the present invention, the method of use involves a regimen that comprises brushing with a dentifrice containing the coolant(s) followed by rinsing with a rinse containing the potentiating agent for the coolant(s). Or the dentifrice may contain the potentiating agent and the rinse will contain the coolant(s). The regimen approach is advantageous for example, when the potentiating agent such as a calcium ion source may present stability problems with components of either the dentifrice or rinse or when there is a desire to delay the onset of the enhancing effect. In addition rinsing would ensure distribution of coolant and potentiating agent throughout the mouth resulting in a whole mouth feeling of refreshing cool sensation. In another embodiment, the regimen comprises brushing or rinsing with a product containing a calcium ion source and/or a calcium transport agent, followed by chewing gum or sucking on a lozenge containing coolant(s) to deliver long lasting cool sensation. Alternatively, the coolant(s) and potentiating agent(s) may be present in all products used in the regimens.

EXAMPLES

The following examples further describe and demonstrate embodiments within the scope of the present invention. These examples are given solely for the purpose of illustration and are not to be construed as limitations of the present invention as many variations thereof are possible without departing from the spirit and scope. Composition ingredients are shown as % by weight unless otherwise indicated.

Example I

Mouthrinse Compositions

Mouthrinse compositions according to the present invention (Ia, Ib and Id to Ij) made using conventional methods and a comparative example Ic are shown below with amounts of components in weight %. Compositions Ia and Ib containing fairly low levels of the G-180 coolant (22.5 ppm and 12.75 ppm) and about 90 ppm calcium ions were judged in sensory testing as providing a cooling sensation that lasted at least 30 minutes. By comparison, mouthrinse formulation (Ic) containing only menthol as coolant and no G-180 and calcium provided lower levels of cooling of shorter duration. Cooling sensation scores for the formulations at various time points are shown below. The potentiating effect of calcium is even more significant given that the mouthrinse formulations contain ethanol which provides a warming effect and would thus be expected to decrease the cooling intensity.

| Ingredient | Ia | Ib | Ic |
|---|---|---|---|
| Ethanol, USP 190 proof | 15.0 | 15.0 | 15.0 |
| Glycerin | 7.5 | 7.5 | 7.5 |
| Polysorbate 80, NF | 0.12 | 0.12 | 0.12 |
| Flavor[1] | 0.16 | 0.16 | 0.16 |
| Saccharin Sodium | 0.067 | 0.067 | 0.06 |
| Color Solution | 0.04 | 0.04 | 0.04 |
| G-180[2] Coolant (7.5% solution) | 0.03 | 0.017 | — |
| Calcium Chloride | 0.025 | 0.025 | — |
| Cetylpyridinium Chloride | 0.045 | 0.045 | 0.045 |
| Benzoic Acid | 0.005 | 0.005 | 0.005 |
| Sodium Benzoate | 0.054 | 0.054 | 0.054 |
| Water | QS | QS | QS |
| Calcium: Coolant Weight Ratio | 4.0 | 7.1 | — |
| Cooling Sensation Scores | | | |
| Elapsed Time | | | |
| 0 minute (After Expectoration) | 29.7 | 26.9 | 25.7 |
| 5 minutes | 31.8 | 26.5 | 26.2 |
| 15 minutes | 25.7 | 18.7 | 13.4 |
| 30 minutes | 17.4 | 9.1 | 4.1 |
| 45 minutes | 8.3 | 5.5 | 1.6 |
| 60 minutes | 3.6 | 2.4 | 0.2 |
| 75 minutes | 1.9 | 1.7 | 0.4 |
| 90 minutes | 0.8 | 1.4 | 0.4 |

| Ingredient | Id | Ie | If | Ig | Ih | Ii | Ij |
|---|---|---|---|---|---|---|---|
| Ethanol, USP 190 proof | 15.0 | 15.0 | 15.0 | 15.0 | 15.0 | 15.0 | 15.0 |
| Glycerin | 7.5 | 7.5 | 7.5 | 7.5 | 7.5 | 7.5 | 7.5 |
| Polysorbate 80, NF | 0.12 | 0.12 | 0.12 | 0.12 | 0.12 | 0.12 | 0.12 |
| Flavor[1] | 0.16 | 0.16 | 0.16 | 0.16 | 0.16 | 0.16 | 0.16 |
| Saccharin Sodium | 0.067 | 0.067 | 0.06 | 0.06 | 0.067 | 0.06 | 0.06 |
| Color Solution | 0.04 | 0.04 | 0.04 | 0.04 | 0.04 | 0.04 | 0.04 |
| G-180[2] (7.5% soln) | 0.03 | 0.017 | — | — | 0.03 | 0.03 | 0.03 |
| Calcium Chloride | 0.025 | 0.025 | — | — | — | — | 0.025 |
| Cetylpyridinium Chloride | 0.045 | 0.045 | 0.045 | 0.045 | 0.045 | 0.045 | 0.045 |
| Benzoic Acid | 0.005 | 0.005 | 0.005 | 0.005 | 0.005 | 0.005 | 0.005 |
| Sodium Benzoate | 0.054 | 0.054 | 0.054 | 0.054 | 0.054 | 0.054 | 0.054 |
| Phytic acid | 0.05 | 0.1 | 0.4 | 3.0 | 0.4 | 3.0 | |
| Alkyl Phosphate[3] (30% soln) | — | — | — | — | 0.50 | — | 0.8 |
| Water | QS | QS | QS | QS | QS | QS | QS |

[1]Flavor comprises about 31.3% menthol supplying about 500 ppm menthol.
[2]G-180 coolant supplied by Givaudan as 7.5% solution in peppermint oil.
[3]Sodium Laureth Phosphate supplied by Rhodia Example II Peroxide Mouthrinse Compositions Peroxide-containing mouthrinse compositions according to the present invention (IIa-IIf) are shown below with amounts of components in weight %. These compositions are made using conventional methods. The mouthrinse compositions provide a pleasant high-impact minty taste during use and noticeable long-lasting fresh breath.

| Ingredient | IIa | IIb | IIc | IId | IIe | IIf |
|---|---|---|---|---|---|---|
| 35% $H_2O_2$ solution | 4.286 | 4.286 | 4.286 | 2.143 | 4.286 | 4.286 |
| Menthol | 0.075 | 0.02 | 0.04 | 0.04 | 0.03 | 0.04 |
| WS-3 Coolant | 0.02 | | 0.02 | 0.02 | | 0.025 |
| WS-23 Coolant | | | | | | 0.01 |
| G-180[1] Coolant (7.5% soln.) | | 0.03 | | | 0.03 | |
| MGA Coolant | | | 0.15 | | | |
| Artificial Mint Flavor[2] | 0.145 | 0.135 | 0.135 | 0.15 | 0.135 | 0.135 |
| Calcium Chloride | 0.025 | | 0.025 | 0.02 | 0.025 | 0.025 |
| Poloxamer 407 | 0.75 | 0.75 | 0.750 | 0.10 | 0.10 | 0.10 |
| Glycerin | 11.00 | 11.00 | 11.00 | 20.00 | 20.00 | 20.00 |
| Propylene Glycol | 3.00 | 3.00 | | 4.00 | 4.00 | 4.00 |
| Sucralose | | 0.05 | — | — | | |

-continued

| Ingredient | IIa | IIb | IIc | IId | IIe | IIf |
|---|---|---|---|---|---|---|
| Sodium Saccharin | 0.08 | — | 0.068 | 0.06 | 0.08 | 0.06 |
| Polyphosphate[3] | | | 1.00 | | | |
| Phytic Acid | | 2.00 | | | | |
| Cetyl Pyridinium Chloride | | | | 0.074 | 0.10 | 0.10 |
| Na Citrate | 0.212 | 0.212 | | | | |
| Citric Acid | 0.052 | 0.052 | 0.052 | | | |
| Alcohol, USP | | | 5.00 | | | |
| Water, Purified, USP | QS | QS | QS | QS | QS | QS |

[1]G-180 supplied by Givaudan as 7.5% solution in peppermint oil.
[2]Artificial Mint Flavor comprises methyl salicylate, cinnnamic alcohol, eucalyptol, menthone and other flavor agents. A mint flavor comprising natural oils (e.g., peppermint, anise, clove bud oil, sweet birch) may be used instead of the artificial mint flavor.
[3]Polyphosphate is Glass H (n ≈ 21) supplied by Astaris.

Example III

Dual-Phase Dentifrice Compositions

Dual phase dentifrice compositions according to the present invention are comprised of a first dentifrice composition (IIIa-IIIc) containing a calcium ion source and a second dentifrice composition (IIId-IIIf) containing ingredients that may interact with calcium such as fluoride, dispensed preferably at a 50:50 ratio. The coolant(s) may be in the first or second dentifrice compositions. These compositions are made using conventional methods.

| | First Dentifrice | | | Second Dentifrice | | |
|---|---|---|---|---|---|---|
| Ingredient | IIIa | IIIb | IIIc | IIId | IIIe | IIIf |
| Glass H Polyphosphate | 7.0 | 7.0 | | | | |
| Calcium Peroxide | 1.0 | | 5.0 | | | |
| Calcium Chloride | | 0.075 | | | | |
| Sodium Fluoride | | | | 0.486 | 0.486 | |
| Stannous Fluoride | | | | | | 0.908 |
| Stannous Chloride | | | | | | 3.0 |
| Sodium Gluconate | | | | | | 4.16 |
| Artificial Mint Flavor[1] | 1.0 | 1.0 | 1.0 | 0.4 | 0.9 | 1.0 |
| Menthol | 0.075 | 0.05 | 0.04 | | | |
| WS-3 Coolant | 0.02 | | 0.02 | | | |
| WS-23 Coolant | | | 0.01 | 0.3 | 0.4 | 0.4 |
| G-180[2] Coolant (7.5% soln.) | | 0.4 | | | | |
| Sodium Saccharin | 0.5 | 0.5 | 0.5 | 0.3 | 0.5 | 0.3 |
| Color Solution | | | | 0.30 | 0.40 | 0.30 |
| Glycerin | 43.2 | 26.8 | 24.2 | 44.5 | 9.0 | 29.0 |
| Sorbitol | | | | | 29.594 | |
| Poloxamer 407 | 5.0 | 5.0 | 5.0 | 21.0 | | 15.5 |
| Polyethylene Glycol | 3.0 | 3.0 | 3.0 | | 3.0 | |
| Propylene Glycol | 5.0 | 5.0 | 5.0 | | | |
| Carboxymethycellulose | 0.6 | 0.6 | 0.6 | | | |
| Carbomer | | | | | 0.2 | |
| Sodium Alkyl Sulfate (27.9% soln) | 4.0 | 4.0 | 4.0 | | 4.0 | |
| Silica Abrasive | 20.0 | 22.0 | 22.0 | | 22.5 | 23.0 |
| Sodium Hydroxide (50% soln.) | | | | | | 1.0 |
| Sodium Bicarbonate | | | 15.0 | | | |
| Sodium Carbonate | 2.0 | 2.0 | 2.0 | | | |
| Titanium Dioxide | 0.5 | 0.5 | 0.5 | | | |
| Xanthan Gum | 0.2 | 0.2 | 0.2 | | 0.6 | |
| Sodium Acid Pyrophosphate | | | | | 0.5 | |
| Tetrasodium Pyrophosphate | | | | | 3.22 | |
| Phytic Acid | | | | 0.2 | 0.8 | 5.0 |
| Water | QS | QS | QS | QS | QS | QS |

[1]Artificial Mint Flavor comprises methyl salicylate, cinnnamic alcohol, eucalyptol, menthone and other flavor agents. A mint flavor comprising natural oils (e.g., peppermint, anise, clove bud oil, sweet birch) may be used instead of the artificial mint flavor.
[2]G-180 supplied by Givaudan as 7.5% solution in peppermint oil.

Example IV

Dentifrice Compositions

Examples IVa to IVn illustrate dentifrice compositions according to the present invention. The compositions may be prepared using conventional methods.

| Ingredient | IVa | IVb | IVc | IVd | IVe | IVf | IVg | IVh | IVi |
|---|---|---|---|---|---|---|---|---|---|
| Calcium Peroxide | | | 0.10 | | | | | | |
| Calcium Chloride | 0.1 | 0.075 | | 0.15 | 0.2 | | | | |
| Carbomer 956 | 0.2 | | | 0.3 | 0.2 | 0.2 | 0.2 | 0.2 | 0.2 |
| CMC | | 0.75 | 0.2 | | | 1.0 | 1.0 | 1.0 | 1.0 |
| Color Solution (1%) | 0.05 | 0.05 | 0.50 | 0.75 | 0.18 | 0.02 | 0.25 | 0.05 | 0.05 |
| Wintergreen Spice Flavor | | | | | 0.15 | | | | |
| Fruit Mint Flavor | | 0.55 | | | | | | | |
| Mint Flavor | 0.59 | | 0.45 | | 0.42 | 1.0 | 1.2 | 1.0 | 1.0 |
| Cinnamon Flavor | | | | 0.5 | | | | | |
| Vanillyl Butyl Ether | | | | | 0.02 | | | | |
| WS-23 | | | 0.02 | 0.05 | 0.02 | | | | |
| WS-3 | | | 0.02 | 0.05 | 0.02 | | | | |
| MGA | | | | 0.2 | | | | | |
| Menthol | 0.52 | 0.55 | 0.56 | 0.15 | 0.58 | | | | |
| G-180 | 0.01 | 0.03 | 0.015 | 0.004 | 0.01 | 0.01 | 0.03 | 0.008 | 0.02 |
| Potassium Sorbate | | | | | | 0.004 | 0.008 | 0.004 | 0.004 |
| Poloxamer 407 | | | 1.0 | | 0.2 | 0.2 | 0.2 | 0.2 | 0.2 |
| Polyethylene Glycol 300 | 3.0 | 3.0 | | 3.00 | | | | | |
| Polyethylene Glycol 600 | | | 2.3 | | | | | | |
| Propylene Glycol | | | 10.0 | | | | | | |
| Saccharin Sodium | 0.46 | 0.5 | 0.45 | 0.4 | 0.58 | 0.4 | 0.4 | 0.4 | 0.4 |
| Sucralose | | | | | | 0.02 | 0.02 | 0.02 | |
| Silica Abrasive | 22.0 | 31.0 | 20.0 | 21.0 | 17.0 | 15.0 | 15.0 | 15.0 | 15.0 |
| Sodium Benzoate | | | | | | 0.004 | 0.004 | 0.004 | 0.004 |
| Silica Thickening | | | 2.0 | | | 7.0 | 7.0 | 7.0 | 7.0 |
| Sodium Bicarbonate | | 1.50 | 9.0 | | | | | | |
| Sodium Carbonate | | 0.50 | | | | | | | |
| NaOH 50% Soln | | | 1.74 | 2.20 | | 2.0 | 2.0 | 2.0 | 2.0 |
| Na Lauryl Sulfate (27.9% soln) | 4.0 | 5.0 | 3.0 | 4.0 | 4.0 | | | 3.0 | 2.0 |
| Sodium Fluoride | | | | | | 0.243 | 0.243 | 0.243 | |
| Sodium MFP | 0.76 | 0.76 | 0.76 | 0.76 | 0.76 | | | | 0.76 |
| Glycerin USP 99.7% | 9.0 | 11.9 | 33.0 | 9.0 | | | | | |
| Sorbitol Soln USP | 24.3 | 24.5 | 4.0 | 44.7 | 56.9 | 43.0 | 43.0 | 40.0 | 38.0 |
| Tetra Na Pyrophosphate, Anhydrous | 2.05 | 5.045 | 3.85 | | 3.85 | | | | |
| Tetra Potassium Pyrophosphate (60% Soln) | 6.38 | | | | | | | | |
| Na Acid Pyrophosphate | 2.1 | | | 4.0 | 1.0 | 4.3 | 4.5 | 4.5 | 2.0 |
| Alkyl Phosphate[3] | | | | | | 3.5 | 6.7 | 3.5 | 3.5 |
| Cocamidopropyl Betaine (30% soln) | | | | | | 3.5 | | | |
| Titanium Dioxide | 0.5 | | 1.0 | | 0.25 | 0.3 | 0.3 | 0.2 | 0.2 |
| TiO$_2$/Carnauba Wax Prills | | 0.6 | | 0.3 | | | | | |
| Xanthan Gum | 0.6 | | 0.4 | 0.45 | 0.7 | 0.3 | 0.3 | 0.3 | 0.3 |
| Water, Purified, USP | QS | QS | QS | QS | QS | QS | QS | QS | QS |

| Ingredient | IVj | IVk | IVl | IVm | IVn |
|---|---|---|---|---|---|
| Calcium Carbonate | | | | 40.0 | |
| Dibasic Calcium Phosphate Dihydrate | | | 35.0 | | |
| Calcium Chloride | 0.05 | | | | |
| Silica Abrasive | 24.0 | 12.5 | | | 17.0 |
| Phytic Acid | | 0.8 | | | 2.0 |
| Gantrez ® S-97 | | | 2.0 | | |
| Color Solution (1%) | 0.05 | 0.05 | | | 0.175 |
| Saccharin Sodium | 0.47 | 0.25 | 0.3 | 0.3 | 0.58 |
| Spice Mint Flavor | | | | 1.0 | |
| Wintergreen Spice Flavor | | 1.2 | | | 0.15 |
| Mint Flavor | 0.3 | | 0.6 | 0.5 | 0.42 |
| Cinnamon Flavor | 0.184 | | | | |
| WS-23 Coolant | 0.03 | | | | 0.02 |
| WS-3 Coolant | 0.03 | | | | 0.02 |
| MGA | 0.08 | 0.08 | | | |
| Menthol | 0.38 | 0.24 | 0.2 | 0.5 | 0.58 |
| G-180 | 0.075 | 0.005 | 0.004 | 0.008 | 0.01 |
| Glycerin | 16.5 | | 15.00 | | |
| Sorbitol Solution | 10.5 | 33.0 | 11.5 | 14.0 | 57.0 |
| Poloxamer 407 | | | | | 0.20 |
| Polyethylene Glycol 300 | | | | 2.5 | |
| Polyethylene Glycol 600 | | | 3.0 | | |
| Carbomer 956 | | 0.3 | | | 0.2 |
| CMC 7M8SF | 1.0 | 1.0 | 1.0 | 1.0 | |

-continued

| | | | | | |
|---|---|---|---|---|---|
| HEC 250MX | | 0.5 | | | |
| Sodium Lauryl Sulfate (27.9% soln) | 7.5 | 7.0 | 5.5 | 7.0 | 4.0 |
| NaOH 50% Soln | | 1.0 | | | |
| Sodium Monofluorophosphate | 0.76 | | 0.76 | 0.76 | 0.76 |
| Sodium Fluoride | | 0.32 | | | |
| Sodium Gluconate | | 1.0 | | | |
| Stannous Chloride Dihydrate | | 1.0 | | | |
| Zinc Citrate | | 0.5 | | | |
| Potassium Nitrate | 5.0 | | | | |
| Sodium Phosphate, Tribasic | 3.2 | | | | |
| Tetra Sodium Pyrophosphate, Anhydrous | | | 0.5 | 0.5 | 3.85 |
| Sodium Acid Pyrophosphate | | | | | 1.0 |
| Titanium Dioxide | 0.5 | 0.5 | | | 0.25 |
| Xanthan Gum (Keltrol 1000) | 0.5 | | | | 0.7 |
| Carrageenan | | 0.5 | | | |
| Water, Purified, USP | QS | QS | QS | QS | QS |

[3]Sodium Laureth Phosphate supplied by Rhodia

Example V

Dentifrice+Rinse Regimen

Example V illustrates a regimen including a dentifrice containing the coolant(s) and a mouthrinse containing the potentiating agent. The regimen may involve first brushing with the dentifrice followed by gargling with either or a mixture of the mouthrinses.

| Dentifrice Ingredient | Wt. % | Rinse Ingredient | A Wt. % | B Wt. % |
|---|---|---|---|---|
| Carrageenan | 0.6 | Ethanol, USP 190 proof | 15.0 | 7.5 |
| Color Solution (1%) | 0.3 | Glycerin | 7.5 | 10.5 |
| Wintergreen Spice Flavor | 0.56 | Polysorbate 80 | 0.12 | 0.12 |
| WS-3 Coolant | 0.09 | Flavor | 0.16 | 0.16 |
| Menthol | 0.35 | Saccharin Sodium | 0.06 | 0.06 |
| G-180 Coolant | 0.015 | Color Solution | 0.04 | 0.04 |
| Polyethylene Glycol 300 | 7.0 | Cetylpyridinium Chloride | 0.045 | 0.045 |
| Propylene Glycol | 7.0 | Benzoic Acid | 0.005 | 0.005 |
| Saccharin Sodium | 0.5 | Sodium Benzoate | 0.054 | 0.054 |
| Silica Abrasive | 25.0 | Phytic Acid | | 0.4 |
| Sodium Gluconate | 0.652 | Water | QS | QS |
| Sodium Lauryl Sulfate | 3.4 | | | |
| Sodium Phosphate, Tribasic | 1.1 | | | |
| Sodium Polyphosphate (Glass H) | 13.0 | | | |
| Stannous Fluoride | 0.454 | | | |
| Xanthan Gum | 0.25 | | | |
| Zinc Lactate Dihydrate | 2.5 | | | |
| Glycerin USP | QS | | | |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of enhancing and/or modulating activity of N-(4-cyanomethylphenyl)-ρ-menthanecarboxamide incorporated in a personal care composition for use on skin, hair, the oral cavity and other mucosal surfaces; a flavor composition or a perfume composition comprising formulating said personal care, flavor and perfume compositions with a calcium ion source and a calcium transport agent, wherein the compositions provide upon use an immediate onset of a pleasant fresh cooling sensation which lasts longer than about 15 minutes and the calcium to coolant ratio is at least about 0.5 to 1 and the calcium transport agent is one or a mixture of a polycarboxylate compound or a phosphate compound selected from a linear polyphosphate having an average chain length of from 3 to about 125; a phytate; organic phosphate mono-, di- or triester; alkali metal, alkaline earth metal or ammonium salts thereof, at a level of at least about 0.1% by weight of the composition.

2. A method according to claim 1 further comprising incorporating menthol in the composition.

3. A personal care composition for use on skin, hair, the oral cavity and other mucosal surfaces comprising
   (a) a flavor or perfume composition comprising N-(4-cyanomethylphenyl)-ρ-menthanecarboxamide,
   (b) a calcium ion source and a calcium transport agent in an amount sufficient to potentiate and/or modulate cooling and other sensory experience provided by the non-menthol coolant(s), and
   (c) a physiologically-acceptable carrier;
   wherein the the calcium to coolant ratio is at least about 0.5 to 1 and the calcium transport agent is one or a mixture of a polycarboxylate compound or a phosphate compound selected from a linear polyphosphate having an average chain length of from 3 to about 125; a phytate; an organic phosphate mono-, di- or triester; alkali metal, alkaline earth metal or ammonium salts thereof, at a level of at least about 0.1% by weight of the composition.

4. An oral care composition comprising
   (a) a flavor composition comprising N-(4-cyanomethylphenyl)-ρ-menthanecarboxamide, (b) a calcium ion source and a calcium transport agent in an amount sufficient to potentiate and/or modulate cooling and refreshing sensation provided by the non-menthol coolant(s), and
(c) an orally-acceptable carrier;
wherein the the calcium to coolant ratio is at least about 0.5 to 1 and the calcium transport agent is one or a mixture of a polycarboxylate compound or a phosphate compound selected from a linear polyphosphate having an average chain length of from 3 to about 125; a phytate; an organic phosphate mono-, di- or triester; alkali metal, alkaline earth metal or ammonium salts thereof, at a level of at least about 0.1% by weight of the composition.

5. An oral care composition according to claim 4 wherein the calcium ion source is an inorganic or organic calcium salt providing at least about 10 ppm $Ca^{+2}$ ions in the composition.

6. An oral care composition according to claim 5 wherein the calcium ion source provides at least about 50 ppm $Ca^{+2}$ ions in the composition.

7. An oral care composition according to claim 5 wherein the calcium ion source provides from about 150 ppm to about 500 ppm $Ca^{+2}$ ions in the composition.

8. An oral care composition according to claim 4 further comprising menthol at a level of at least about 0.01% by weight of the composition.

* * * * *